(12) United States Patent
Gall et al.

(10) Patent No.: US 10,568,316 B2
(45) Date of Patent: Feb. 25, 2020

(54) APPARATUS AND METHODS FOR IN-FIELD DATA COLLECTION AND SAMPLING

(71) Applicant: Monsanto Technology LLC, St. Louis, MO (US)

(72) Inventors: Michael Gall, St. Louis, MO (US); Edward Carter, St. Louis, MO (US); Haitao Xiang, St. Louis, MO (US); Kevin Deppermann, St. Louis, MO (US); Steven J. Baldwin, St. Louis, MO (US); Thomas W. Christian, St. Louis, MO (US); Susan A. Macisaac, St. Louis, MO (US); Akash D. Nakarmi, St. Louis, MO (US); Boyan N. Peshlov, St. Louis, MO (US); Beiyan Zeng, St. Louis, MO (US)

(73) Assignee: MONSANTO TECHNOLOGY LLC, Saint Louis, MO (US)

( * ) Notice: Subject to any disclaimer, the term of this patent is extended or adjusted under 35 U.S.C. 154(b) by 327 days.

(21) Appl. No.: 15/502,548

(22) PCT Filed: Aug. 14, 2015

(86) PCT No.: PCT/US2015/045301
§ 371 (c)(1),
(2) Date: Feb. 8, 2017

(87) PCT Pub. No.: WO2016/025848
PCT Pub. Date: Feb. 18, 2016

(65) Prior Publication Data
US 2017/0223947 A1 Aug. 10, 2017

Related U.S. Application Data

(60) Provisional application No. 62/037,968, filed on Aug. 15, 2014.

(51) Int. Cl.
*A01B 79/00* (2006.01)
*A01M 7/00* (2006.01)
(Continued)

(52) U.S. Cl.
CPC ......... *A01M 7/0089* (2013.01); *A01B 79/005* (2013.01); *G01N 21/4738* (2013.01);
(Continued)

(58) Field of Classification Search
CPC ........................... A01B 79/005; A01M 7/0089
See application file for complete search history.

(56) References Cited

U.S. PATENT DOCUMENTS

2012/0109614 A1 5/2012 Lindores
2012/0113225 A1 5/2012 Deppermann et al.
(Continued)

OTHER PUBLICATIONS

International Search Report from corresponding PCT/US2015/045301 dated Nov. 4, 2015.

*Primary Examiner* — Kristen C Hayes
(74) *Attorney, Agent, or Firm* — Sandberg Phoenix & von Gontard PC

(57) ABSTRACT

A mobile platform structured and operable to perform: in-field phenotype and/or genotype data acquisition; image data acquisition; tissue sampling; selection and/or counting of plants growing in a plot; plant height measurement; product and treatment application to plants growing in the plot (e.g., prescriptive and localized insecticide products); sampling of soil where such plants are growing; removal of weeds in such plots; and real-time analysis of all such data and/or samples acquired/collected. Additionally, when combined with location positioning technology and path planning, such a vehicle is further structured and operable to re-enter a field numerous times throughout a season to
(Continued)

accurately and repeatably monitor growing conditions, plant response or prescriptive application of a product.

5 Claims, 11 Drawing Sheets

(51) Int. Cl.
    *G01N 21/47*     (2006.01)
    *G01N 27/04*     (2006.01)
    *G01N 27/414*     (2006.01)
    *G01N 33/24*     (2006.01)
    *G06T 7/00*     (2017.01)

(52) U.S. Cl.
    CPC ......... *G01N 27/043* (2013.01); *G01N 27/414* (2013.01); *G01N 33/24* (2013.01); *G01N 2033/245* (2013.01); *G06T 7/0004* (2013.01); *G06T 2207/30188* (2013.01)

(56) References Cited

U.S. PATENT DOCUMENTS

| | | |
|---|---|---|
| 2013/0197806 A1 | 8/2013 | Belzer et al. |
| 2013/0325242 A1 | 12/2013 | Cavender-Bares et al. |
| 2014/0168412 A1 | 6/2014 | Shulman et al. |

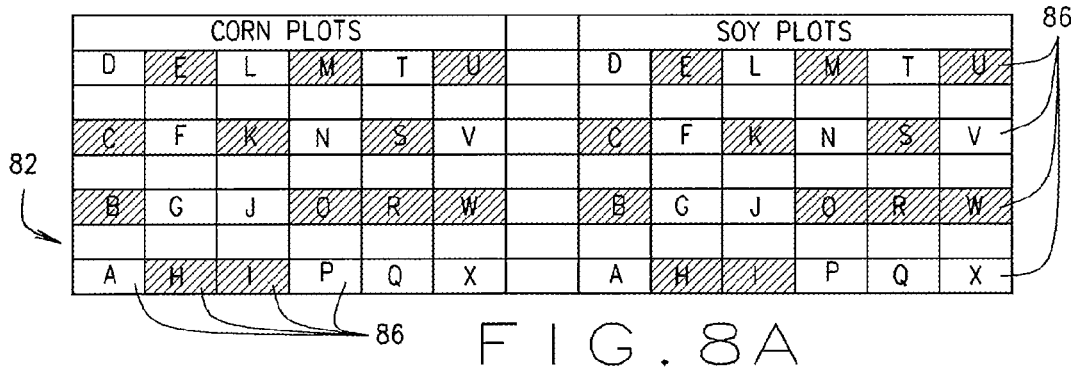
FIG. 8A
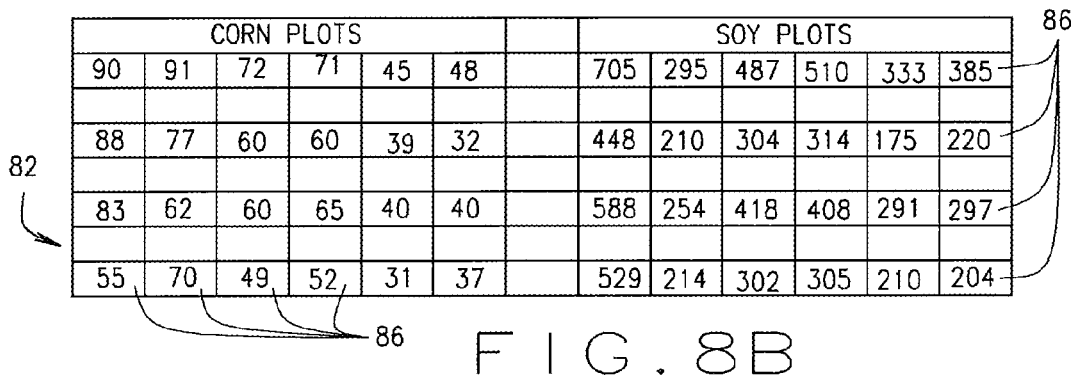
FIG. 8B
| CROP | CROP | LAI vs NDVI | LAI vs STAND | NDVI vs STAND |
|------|------|-------------|--------------|---------------|
| CORN | MEDIAN r | 0.59 | 0.77 | 0.60 |
|      | RANGE | 0.37 TO 0.75 | 0.48 TO 0.80 | 0.49 TO 0.70 |
| SOY  | MEDIAN r | 0.48 | 0.95 | 0.30 |
|      | RANGE | 0.43 TO 0.58 | 0.94 TO 0.96 | 0.26 TO 0.44 |
FIG. 8C
| | AREA | | NDVI | |
|---|---|---|---|---|
| CROP | MEAN | CV | MEAN | CV |
| CORN | 5.06 | 7.6 | 0.244 | 1.1 |
| SOY | 14.51 | 1.5 | 0.348 | 0.9 |
FIG. 8F
| | AREA | |
|---|---|---|
| CROP | MEAN | CV |
| CORN | 5.06 | 7.6 |
| SOY | 14.51 | 1.5 |
FIG. 8H

| CROP | PLOT | STAND | AREA | | NDVI | |
|---|---|---|---|---|---|---|
| | | | MEAN | CV | MEAN | CV |
| CORN | A | 55 | 2.49 | 9.1 | 0.2485 | 0.9 |
| CORN | D | 90 | 10.38 | 40.2 | 0.2572 | 0.5 |
| CORN | F | 77 | 11.54 | 10.7 | 0.2455 | 0.5 |
| CORN | G | 62 | 4.25 | 11.9 | 0.2479 | 0.9 |
| CORN | J | 60 | 3.89 | 2.4 | 0.2435 | 1.0 |
| CORN | L | 72 | 12.50 | 10.3 | 0.2496 | 1.0 |
| CORN | N | 60 | 6.02 | 4.2 | 0.2439 | 1.1 |
| CORN | P | 52 | 2.17 | 3.1 | 0.2333 | 1.1 |
| CORN | Q | 31 | 3.03 | 2.2 | 0.2414 | 1.4 |
| CORN | T | 45 | 2.89 | 3.9 | 0.2363 | 1.0 |
| CORN | V | 32 | 2.10 | 9.4 | 0.2461 | 1.1 |
| CORN | X | 37 | 1.70 | 10.6 | 0.2449 | 1.6 |

| CROP | PLOT | STAND | AREA | | NDVI | |
|---|---|---|---|---|---|---|
| | | | MEAN | CV | MEAN | CV |
| SOY | B | 588 | 24.31 | 1.7 | 0.3704 | 1.0 |
| SOY | D | 705 | 32.78 | 0.9 | 0.3691 | 0.6 |
| SOY | F | 210 | 7.38 | 2.0 | 0.3748 | 0.7 |
| SOY | G | 254 | 11.38 | 2.0 | 0.3789 | 1.1 |
| SOY | I | 302 | 11.46 | 2.1 | 0.3399 | 0.6 |
| SOY | L | 487 | 18.39 | 1.0 | 0.3435 | 0.6 |
| SOY | N | 314 | 11.18 | 2.3 | 0.3432 | 0.5 |
| SOY | O | 408 | 16.90 | 2.1 | 0.3451 | 1.1 |
| SOY | R | 291 | 9.38 | 1.1 | 0.3217 | 0.6 |
| SOY | T | 333 | 8.55 | 6.6 | 0.3113 | 2.0 |
| SOY | V | 220 | 7.03 | 0.4 | 0.3174 | 1.7 |
| SOY | X | 204 | 7.41 | 1.0 | 0.3250 | 1.2 |

FIG. 8D

APPARATUS AND METHODS FOR IN-FIELD DATA COLLECTION AND SAMPLING

CROSS-REFERENCE TO RELATED APPLICATIONS

This application is a National Stage of International Application No. PCT/US2015/045301, filed Aug. 14, 2015, which claims priority to, which claims priority to U.S. Provisional Application No. 62/037,968, filed on Aug. 15, 2014, the disclosures of which are incorporated herein by reference in its entirety.

FIELD

The present teachings relate to mobile platforms for in-field collection of plant data and samples, and real-time analysis of all such data and/or samples acquired and collected.

BACKGROUND

The statements in this section merely provide background information related to the present disclosure and may not constitute prior art.

Various crop improvement programs require large and meticulous selection processes that effectively and accurately collect and analyze data in order to generate quality plant products as efficiently as possible and/or to develop superior cropping and/or crop improvement methods. For example, a microbial or plant improvement program typically requires a large and effective selection process to accurately select the types of microbes or plant germplasms that perform the best. In order to make very accurate selections, thousands of microbe formulations must be tested on thousands of plants to reduce the errors associated with environment, human mistakes, genetics of the plants and microbes studied, etc. Typically, data acquisition and sample collection for such testing is currently performed by hand by teams of people walking through a field using hand-held instruments and/or using individual manually-controlled devices. Although steps are taken to reduce error, the data collected in such a manner can be unreliable due to human error and fatigue, which reduces the ability to make accurate selection decisions.

SUMMARY

The present teachings relate to a mobile platform (e.g., a terrestrial and/or an aerial vehicle) structured and operable to perform: chemical, physical, and biological data acquisition, including phenotyping, genotyping, and biochemical assessments of plants, animals, or microbes; image data acquisition (e.g., NIR and/or multi-spectral image data); tissue sampling; selection and/or counting of plants growing in a plot; plant height measurement; product and treatment application to plants growing in the plot (e.g., prescriptive and localized insecticide products); sampling of soil where such plants are growing (e.g., sample soil for soil composition or nutrient characterization); removal of weeds in a growing area (e.g., an area other than where the plants are in a plot and/or the surrounding area); real-time analysis of all data and/or samples acquired/collected, and real-time implementation of response actions based on the real-time analysis. Additionally, when combined with location detection technology and path planning, such a vehicle is further structured and operable to re-enter a field numerous times throughout a season to accurately and repeatably monitor growing conditions, plant response or prescriptive application of a product.

Further areas of applicability of the present teachings will become apparent from the description provided herein. It should be understood that the description and specific examples are intended for purposes of illustration only and are not intended to limit the scope of the present teachings.

DRAWINGS

The drawings described herein are for illustration purposes only and are not intended to limit the scope of the present teachings in any way.

FIGS. 8A through 8H illustrate exemplary test results and data collected utilizing the automated crop analysis and treatment system shown in FIG. 1, in accordance with various embodiments of the present disclosure.

Corresponding reference numerals indicate corresponding parts throughout the several views of drawings.

DETAILED DESCRIPTION

Figure 1:
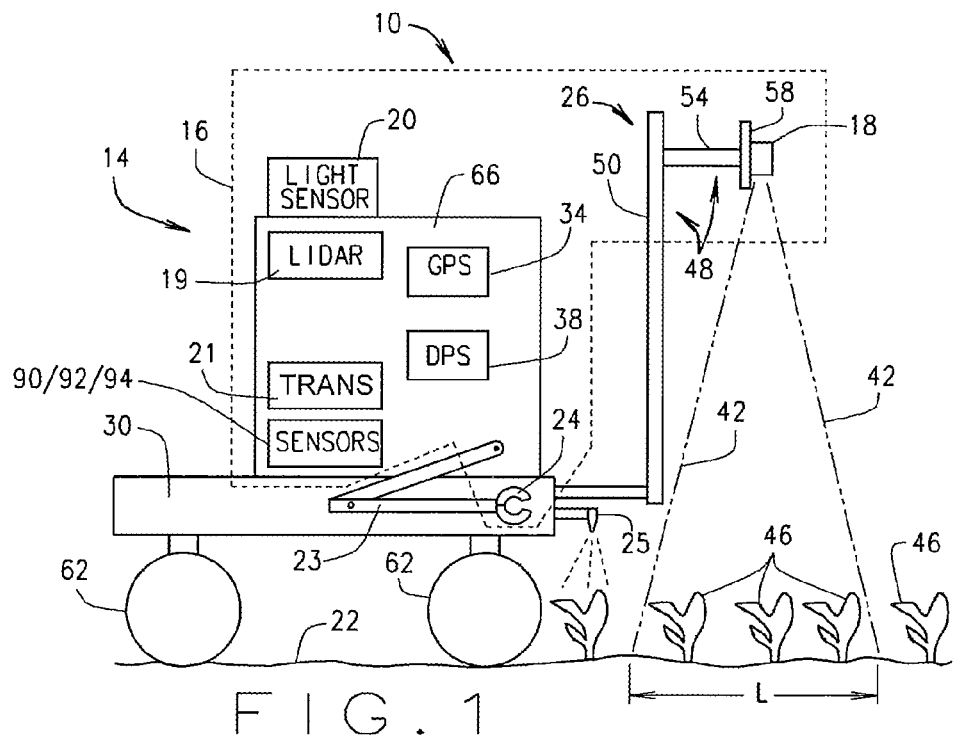
FIG. 1 is a schematic side view of an automated crop analysis and treatment system, in accordance with various embodiments of the present disclosure.

The following description is merely exemplary in nature and is in no way intended to limit the present teachings, application, or uses. The embodiments disclosed below are not intended to be exhaustive or to limit the invention to the precise forms disclosed in the following detailed description. Rather, the embodiments are chosen and described so that others skilled in the art can utilize their teachings. Throughout this specification, like reference numerals will be used to refer to like elements.

Unless otherwise defined, all technical and scientific terms used herein have the same meaning as commonly understood by one of ordinary skill in the art to which this disclosure belongs. The terminology used herein is for the purpose of describing particular example embodiments only and is not intended to be limiting. As used herein, the singular forms "a," "an," and "the" may be intended to include the plural forms as well, unless the context clearly indicates otherwise. The terms "comprises," "comprising," "including," and "having," are inclusive and therefore specify the presence of stated features, integers, steps, operations, elements, and/or components, but do not preclude the presence or addition of one or more other features, integers, steps, operations, elements, components, and/or groups thereof. The method steps, processes, and operations described herein are not to be construed as necessarily requiring their performance in the particular order discussed or illustrated, unless specifically identified as an order of performance. It is also to be understood that additional or alternative steps can be employed.

When an element or layer is referred to as being "on," "engaged to or with," "connected to or with," or "coupled to or with" another element, device, object, etc., it can be directly on, engaged, connected or coupled to or with the other element, device, object, etc., or intervening elements, devices, objects, etc., can be present. In contrast, when an element is referred to as being "directly on," "directly engaged to," "directly connected to," or "directly coupled to" another element, device object, etc., there may be no intervening elements, devices, objects, etc., present. Other words used to describe the relationship between elements should be interpreted in a like fashion (e.g., "between" versus "directly between," "adjacent" versus "directly adjacent," etc.). As used herein, the term "and/or" includes any and all combinations of one or more of the associated listed items.

Although the terms first, second, third, etc. can be used herein to describe various elements, components, regions, devices, objects, sections, etc., these elements, components, regions, devices, objects, sections, etc., should not be limited by these terms. These terms may be used only to distinguish one element, component, region, device, object, section, etc., from another region, device, object, section etc., and do not necessarily imply a sequence or order unless clearly indicated by the context.

The term code, as used herein, can include software, firmware, and/or microcode, and can refer to one or more programs, routines, functions, classes, and/or objects. The term shared, as used herein, means that some or all code from multiple modules can be executed using a single (shared) processor. In addition, some or all code from multiple modules can be stored by a single (shared) memory. The term group, as used above, means that some or all code from a single module can be executed using a group of processors. In addition, some or all code from a single module can be stored using a group of memories.

As described below, the apparatuses/systems and methods described herein can be implemented by one or more computer programs executed by one or more processors. The computer programs include processor-executable instructions that are stored on a non-transitory, tangible, computer-readable medium. The computer programs can also include stored data. Non-limiting examples of the non-transitory, tangible, computer-readable medium are nonvolatile memory, magnetic storage, and optical storage.

As used herein, a microbe will be understood to be a microorganism, i.e. a microscopic living organism, which can be single celled or multicellular. Microorganisms are very diverse and include all the bacteria, archea, protozoa, fungi, and algae, especially cells of plant pathogens and/or plant symbiots. Certain animals are also considered microbes, e.g. rotifers. In various embodiments, a microbe can be any of several different microscopic stages of a plant or animal. Microbes also include viruses, viroids, and prions, especially those which are pathogens or symbiots to crop plants.

As used herein the term plant refers to a whole plant, any part thereof, or a cell or tissue culture derived from a plant, comprising any of: whole plants, plant components or organs (e.g., leaves, stems, roots, etc.), plant tissues, seeds, plant cells, and/or progeny of the same. A plant cell is a biological cell of a plant, taken from a plant or derived through culture from a cell taken from a plant.

As used herein the term Fungus refers to a whole fungus, any part thereof, or a cell or tissue culture derived from a fungus, comprising any of: whole fungus, fungus components or organs, fungal tissues, spores, fungal cells, including cells of hyphae and/or cells of mycelium, and/or progeny of the same. A fungus cell is a biological cell of a fungus, taken from a fungus or derived through culture from a cell taken from a fungus.

As used herein the phrase population of plants or plant population means a set comprising any number, including one, of individuals, objects, or data from which samples are taken for evaluation, e.g. estimating QTL effects and/or disease tolerance. Most commonly, the terms relate to a breeding population of plants from which members are selected and crossed to produce progeny in a breeding program. A population of plants can include the progeny of a single breeding cross or a plurality of breeding crosses, and can be either actual plants or plant derived material, or in silico representations of the plants. The population members need not be identical to the population members selected for use in subsequent cycles of analyses or those ultimately selected to obtain final progeny plants. Often, a plant population is derived from a single biparental cross, but can also derive from two or more crosses between the same or different parents. Although a population of plants can comprise any number of individuals, those of skill in the art will recognize that plant breeders commonly use population sizes ranging from one or two hundred individuals to several thousand, and that the highest performing 5-20% of a population is what is commonly selected to be used in subsequent crosses in order to improve the performance of subsequent generations of the population As used herein the term tolerance or improved tolerance in a plant to disease conditions will be understood to mean an indication that the plant is less affected by disease conditions with respect to yield, survivability and/or other relevant agronomic measures, compared to a less tolerant, more "susceptible" plant. Tolerance is a relative term, indicating that a "tolerant" plant survives and/or produces better yields in disease conditions compared to a different (less tolerant) plant (e.g., a different corn line strain) grown in similar disease conditions. As used in the art, disease "tolerance" is sometimes used interchangeably with disease "resistance." One of skill in the art will appreciate that plant tolerance to disease conditions varies widely, and can represent a spectrum of more-tolerant or less-tolerant phenotypes. However, by simple observation, one of skill in the art can generally determine the relative tolerance or susceptibility of different plants, plant lines or plant families under disease conditions, and furthermore, will also recognize the phenotypic gradations of "tolerant."

As used herein, crop or plant performance is a metric of how well a crop plant grows under a set of environmental conditions and cultivation practices. Crop/plant performance can be measured by any metric a user associates with a crop's productivity (e.g. yield), appearance and/or robustness (e.g. color, morphology, height, biomass, maturation rate), product quality (e.g. fiber lint percent, fiber quality, seed protein content, seed carbohydrate content, etc.), cost of goods sold (e.g. the cost of creating a seed, plant, or plant product in a commercial, research, or industrial setting) and/or a plant's tolerance to disease (e.g. a response associated with deliberate or spontaneous infection by a pathogen) and/or environmental stress (e.g. drought, flooding, low nitrogen or other soil nutrients, wind, hail, temperature, day length, etc.). Crop/plant performance can also be measured by determining a crop's commercial value and/or by determining the likelihood that a particular inbred, hybrid, or variety will become a commercial product, and/or by determining the likelihood that the offspring of an inbred, hybrid, or variety will become a commercial product. Crop/plant performance can be a quantity (e.g. the volume or weight of seed or other plant product measured in liters or grams) or some other metric assigned to some aspect of a plant that can be represented on a scale (e.g. assigning a 1-10 value to a plant based on its disease tolerance).

Referring to FIG. 1, the present disclosure provides an automated crop analysis and treatment system 10 that is structured and operable to move through or over a field and: 1) map the location of every sample it collects and every plant growing in the field; 2) acquire various types of image data of each plant, or selected groups of plants (e.g., two-dimensional (2D) image data, three-dimensional (3D) image data and line-scan image data); 3) acquire various biochemical and/or genotypic and/or phenotypic and/or crop performance data from a plant, animal, and/or microbe or a selected group thereof; 4) collect cells or tissues of a plant, animal, and or microbe and/or samples of soil or air; 5) analyze, in real-time, the acquired data and collected samples in real-time to determine one or more biochemical, genotypic, phenotypic, or environmental characteristics of the plants, animals, and/or microbes and/or growing environment; 6) determine, in real-time, a desired course of action based on the analysis; 7) carryout the determined course of action, and; 8) record and store the captured data, collected samples, resulting analysis, course of action taken, and mapped location for future reference and use. As used herein, the term air will be understood to mean the composition of gasses in the atmosphere of the growing area (e.g., an area other than where the plants are in a plot and/or the surrounding area).

More specifically, the system 10 is structured and operable to simultaneously acquire or capture genotype and/or phenotype data (e.g., 2D, 3D or line-scan color and/or near infrared (NIR) images of the plants), map the location of each plant (e.g., via GPS), collect environmental samples and data, e.g., air and soil samples and/or light index or luminosity (e.g., sun intensity) and/or wind direction and speed and/or temperature and/or humidity and/or time of day and/or time of year, etc., as the system 10 travels through or over an area intended for crop cultivation, e.g., down or over the rows of plants. Subsequently, the system 10 analyzes the acquired/captured data and collected samples in real-time and determines, detects and/or quantifies one or more characteristic of a plant, animal, and/or microbe, and/or detects and/or quantifies one or more characteristics of the environment (e.g., analyzes a soil or air/gas sample) in, on, or near an area of agricultural use, e.g. a growing area for crops. Then, based on the analysis, the system 10, via execution of one or more algorithms, locally or remotely, determines and carries out a desired course of action, e.g., take no action: deactivate one or more plants, rows or plots; spray one or more plants with an herbicide or pesticide; obtain a tissue (e.g., plant tissue), soil or air sample; perform further analysis, etc., utilizing the acquired/captured data and pre-existing data and information stored locally and/or remotely.

Figure 2:
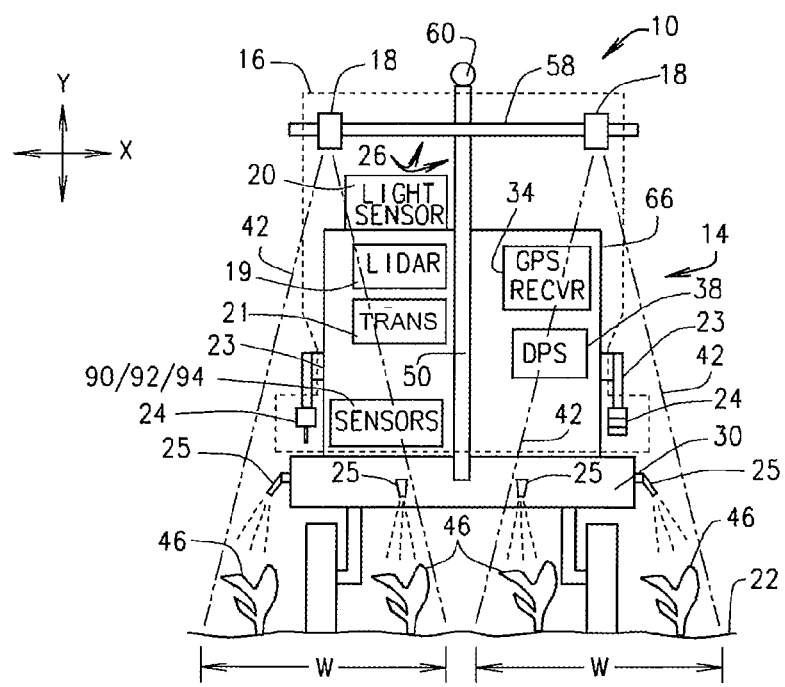
FIG. 2 is a schematic front view of the automated crop analysis and treatment system shown in FIG. 1, in accordance with various embodiments of the present disclosure.
Figure 3:
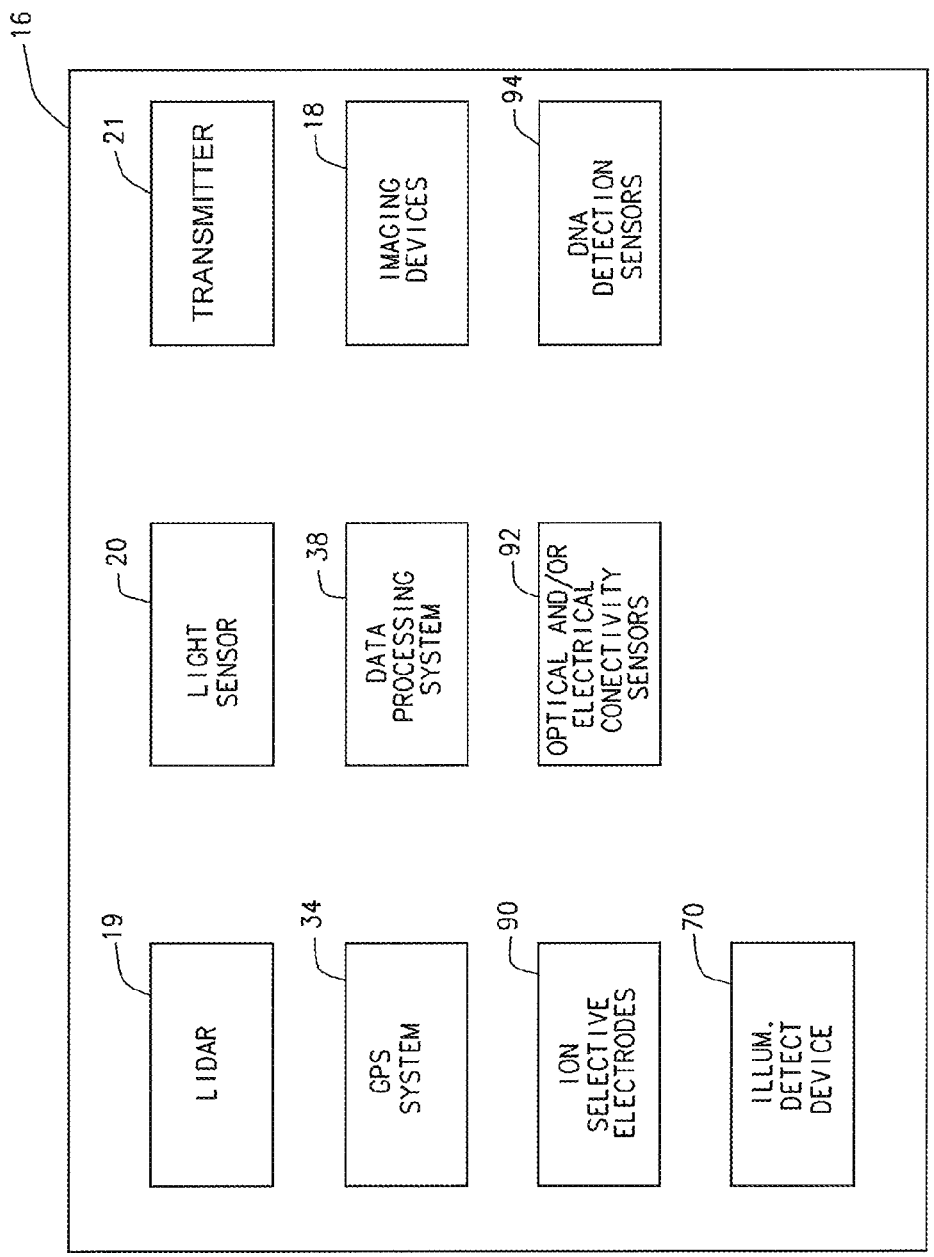
FIG. 3 is a block diagram of an analytics suite of the automated crop analysis and treatment system shown in FIG. 1, in accordance with various embodiments of the present disclosure.

Referring now to FIGS. 1, 2 and 3, generally the system 10 includes a self-propelled mobile platform 14, a data processing system 38 and an analytics suite 16 disposed on the mobile platform 14. The analytics suite 16 comprises various data and sample gathering, collecting and capturing devices, and various data analysis devices. For example, in various embodiments, the analytics suite 16 includes one or more imaging devices 18 suspended above a ground surface 22 by a imaging device suspension and positioning assembly 26 mounted to a chassis 30 of the mobile platform 14, a location positioning system 34 (e.g., a GPS receiver and corresponding display or any other suitable location positioning system), and at least a portion of the computer based data processing system 38 that is communicatively connected to the imaging device(s) 18, the location positioning system 34 and various other components of the analytics suite 16. The imaging device(s) 18 can comprise any one or more and any combination of one or more multi-spectral camera, hyper-spectral camera, NIR spectrometer, 3-dimensional camera, RGB camera, or any other imaging device. Additionally, in various embodiments, the analytics suite 16 can include an illumination detection device 70 (FIG. 4) mounted to the imaging device suspension and positioning assembly 26; a light imaging detection and ranging (LIDAR) device 19 for measuring various distances and/or plant dimensions such as plant height; an illumination meter or light sensor 20 for measuring the natural sun light intensity; and a wireless data transmitter 21, e.g., a transmitter or wireless gateway, for communicating various information and data to a remote receiver. In yet further embodiments, the analytics suite 16 can include at least one ion selective electrode 90 for testing or sampling soil, at least one optical and/or electrical conductivity sensor 92 for testing or sampling soil, and/or at least one deoxyribonucleic acid (DNA) detection sensor 94 for testing or sampling soil. In still other embodiments, the analytics suite 16 can utilize sunlight or active lighting such as LEDs as light sources for imaging. In various implementations the system 10 can include a canopy to reduce the impact of shadows and sunlight intensity/direction on the image field.

The system 10 additionally includes various treatment and solution applicators 25, and other robotic appendages 23 mounted or connected to the mobile platform 14 for obtaining various data to be analyzed and carrying out any determined course of action (as described below). For example, in various embodiments the robotic appendages 23 can comprise one or more robotic articulating arms having interchangeable tools 24 removably connectable to a distal end thereof for collecting plant, air and/or soil samples and/or carrying out the determined course(s) of action. The interchangeable tools 24 can include such things as a claw for grasping plants, a hypodermic needle injecting plants with a solution (e.g., an infestation solution), a knife for pruning plants or removing tissue samples from plant, and/or a leaf tissue punch for removing tissue samples from plants. The interchangeable tools 24 can also include components of the analytics suite 16 such as the ion selective electrodes 90 for testing or sampling soil, the optical or electrical conductivity sensors 92 for testing or sampling soil, and the DNA detection sensors 94 for testing or sampling soil. Additionally, the treatment and solution applicators 25 can comprises spray nozzle(s), etc., operable to apply selected solutions such as water, pesticides, herbicides, agar solutions, etc., to one or more selected plants 48 and/or plots 86 and/or fields 82.

It is envisioned that the system 10 and/or analytics suite 16 can incorporate any other analytical and/or scientific device, subsystem, apparatus, mechanism or tool disposed on or mounted/connected to the mobile platform 14 for interactively testing and/or capturing and/or collecting and/or analyzing information from a growing area. This interactive testing can include, but is not limited to, the collection of cells, tissues, organs, or whole organisms of plants, animals, microbes, insects and/or other living things growing in, on, or near a growing area, as well as the collection of soil or air samples in or near a growing area. For example, the system 10 can be configured with at least one saw on at least one appendage capable of cutting out a section of a corn stalk, e.g. a small circular saw makes two lateral cross cuts through the stalk at some distance from one another such that a section of some length desired by the user is freed form the stalk. Other appendages could be configured with grasping tools that can recover the cut section and bring it onboard the platform 10 for analysis, or transport the section of stalk to another location. Other tissues or organs can be collected from a plant in this way, or using different types of blades, saws, and/or grasping appendages depending biological constraints and/or the specific requirements of the testing that will be conducted on the tissue, and/or how the tissue needs to be collected, for example, a picker that removes seed pods from a soybean plant. In various embodiments, appendages can be configured that would permit the system 10 to take a small piece of tissue, such as a leaf-punch, seed, anther, root, ear, or other plant tissue or organ. In various embodiments, the appendages can be configured to collect pollen, seeds, or other tissues. In various embodiments, the appendages can be configured with tools capable of extracting tissue and/or nucleic acids from an embryo or endosperm (e.g. seed chipping) to determine the sequence of a nucleic acid in the embryo or endosperm before the embryo or endosperm is harvested from the plant or removed from the growing area.

Similarly, appendages can be configured to collect soil in substantially any way, including by taking "plugs", i.e. a vertical cylinder of soil, or samples comprising strips of soil of specified width, length, and or depth.

In various embodiments, appendages can also be configured to collect samples of chemicals in gaseous forms, i.e. "air" samples. For example, appendages can be configured with various filters, and/or vacuums, and/or spectrometers, anemometers, and/or light sources, and/or filters that permit the system 10 to detect, quantify, and/or collect and/or concentrate chemicals present in the growing area. In various embodiments, an appendage can be equipped with any type of chemosensory technology, e.g. photo-ionization detection, (micro) gas chromatography, or any other type of electronic nose technology that facilitates the detection and/or quantification of chemicals. In various embodiments, the system 10 can make use of one or more of these technologies to detect and quantify volatile organic compounds (VOCs) originate from a plant, microbe, insect, or other living thing in, on, or near a growing area.

This interactive testing can also include assays performed on the environment (e.g., samples of soil and/or air) or a plant, animal, microbe, insect, and/or other living thing in, on, or near a growing area. In various embodiments, the system can apply a treatment to a tissue, plant, microbe, and/or insect, etc, and then collect data related to the effects of the treatment. For example, the system 10 can be configured with appendages capable of injecting a plant with a pathogen, and configured with appendages capable capturing optical and/or image data related to how the treatment affected the growth of soil microbes growing near the plant over time and/or the effects of the treatment on crop performance in the growing area.

It is also envisioned that the system 10 and/or analytics suite 16 can incorporate any other analytical and/or scientific device, subsystem, apparatus, mechanism or tool disposed on or mounted/connected to the mobile platform 14 for passively testing and/or capturing and/or collecting and/or analyzing information from a growing area. This passive testing can include, but is not limited to, the use of imaging or optical instruments to capture electromagnetic data and/or measure any attribute of an animal, plant, microbe, insect and/or or other living thing growing in, on, or near a growing area, as well as the use of imaging instruments to image and/or measure any attribute of the soil or air in or near a growing area. Examples of data that can be collected passively using imaging and/or optical equipment include measuring biomass, flower/inflorescence size or shape, internode length, leaf angle, amount of necrotic tissue area, or any other characteristic that an image system can be designed to detect and/or distinguish and/or quantify.

Furthermore, it is envisioned that the system 10 and/or analytics suite 16 can incorporate any other analytical and/or scientific device, subsystem, apparatus, mechanism or tool disposed on or mounted/connected to the mobile platform 14 that a user deems useful for interactively or passively analyzing the environment, and/or a plant, animal, microbe, insect and/or other living thing in a growing area. These analyses include, but are not limited to any biochemical assay of the environment or living things in a growing area, including DNA sequencing and/or genotyping, phenotyping on a plant, animal, microbe, or insect. In various embodiments a whole organism can be processed in an analysis. For example, it is envisioned that substantially all insects of a given species that are growing on a plant can be collected by the system 10 and then counted and/or subjected to a biochemical analysis to detect and/or quantify one or more chemicals in the collective tissues of the insects captured. In various embodiments, a whole plant can be collected including the roots and the plant body reoriented and placed into at least one analytical device on the platform that analyzes some aspect of the plant and/or a microbe and/or insect growing on the plant. In various embodiments, plant pathogens residing in the soil, air, and/or on the plants themselves can be detected, quantified, and assayed by the system 10. In various embodiments, the system 10 can detect, collect, count, and/or assay plant material in a growing area for traits related to plant residue silage quality.

In various embodiments, the system 10 can use the analytics suite to determine such things as stand count, plant height, yield, crop performance characteristics (e.g., the severity of disease in a plant or group of plants, plant disease levels, plant infestation levels, disease resistance, etc.), and soil characterization or soil nutrient composition. Additionally, in various embodiments, the system 10 can use the analytics suite to characterize a sample of soil or air based on its moisture level, temperature, and/or nutrient composition. Furthermore, the system 10 and/or analytics suite 16 can incorporate any other analytical and scientific device, subsystem, apparatus, mechanism or tool disposed on or mounted/connected to the mobile platform 14 for carrying out any desired course of action determined by such data analysis.

Although the mobile platform 14 is exemplarily illustrated throughout the various figures as a terrestrial vehicle, e.g., a manned or unmanned terrestrial vehicle, it is envisioned that the mobile platform 14 can be a manned or unmanned aerial vehicle, e.g., a remote controlled aerial vehicle, and remain within the scope of the present disclosure. More specifically, the mobile platform 14 can be any manned or unmanned terrestrial or aerial vehicle structured and operable to traverse a field, e.g., a test plot, or other specified area. However, for clarity and simplicity, the mobile platform 14 will be exemplarily described herein as an unmanned terrestrial vehicle.

For example, in such exemplary embodiments, the mobile platform 14 can be a lightweight terrestrial vehicle that is easily transportable from one location to another, e.g., can be towed on a trailer connected to a pickup truck or transported on a flatbed truck or larger truck without any oversized load requirements, such as a modified mobile high clearance sprayer. Furthermore, in various embodiments, the mobile platform 14 can comprise a low impact self-propelled platform that minimizes soil compaction of the ground surface 22 by being a lightweight vehicle with large diameter tires for increased soil floatation. Still further, in various embodiments, the mobile platform 14 can include narrow tires such that crop disturbance is minimized for all growth stages, adjustable wheel spacing that accommodates row widths from 20 to 40 inches, and articulated steering leaving only two tire tracks for both straight line and through tight turns. Further yet, in various embodiments, the mobile platform 14 can be structured to have an adjustable height chassis that provides up to 60 inches of ground clearance and a narrow drive system that fits between the rows of plants such that plant canopy disturbance of mature plants is minimized. Still further yet, in various embodiments, the mobile platform 14 can comprise a hydrostatic drive including 4-wheel drive and a variable speed transmission to provide traction in adverse field conditions while maintaining optimum engine power.

In various embodiments, via the location positioning system 34 and the computer based data processing system 38, the mobile platform 14 is structured and operable to follow a pre-planned path, provided by designated planting software, through the field. In various embodiments, the system 10 can calibrate the actual location (e.g., GPS coordinates) of a field to be analyzed such that pre-programmed location data (e.g., GPS coordinates) of the field(s), plot(s), row(s), alleys, plants, etc. will accurately identify the actual location of the field(s), plot(s), row(s), alleys, plants, etc., and thus the data acquired by the system 10 during operation can be accurately correlated with the geospatial location at which each bit of data is collected. For example, in various embodiments, prior to the operation to acquire and analyze data, the system 10 can move along the perimeter of one or more fields and/or plots to be analyzed, and record/map the locations (e.g., GPS locations) at the four corners of the one or more fields and/or plots, thereby creating a geo-fence or map of the field and/or each plot within the field. Thereafter, the system 10 can track its location in the respective field(s) and/or plot(s), and calibrate the geospatial data that will be used to instruct the system 10 to collect other information, such that the instructional geospatial data will be accurate with regard to the actual position of the system 10 in field, and importantly the position of each plant and/or sample, during acquisition of the various data, samples, etc., as described herein. As a result, every time the mobile platform 14 enters a field or plot, the location, orientation, shape, topography and dimensions of the field or plot is known. Therefore, images (e.g., 2D, 3D or line-scan images) and other data can be captured and collected for the same plot multiple times throughout the season. Furthermore, in various implementations, the pass-to-pass position can be 1-3 inches, e.g., 2 inches, thereby enabling precise location tracking and sufficient resolution to map each plot region in the field.

In various embodiments, once the images and data are captured and analyzed, a researcher can track such things as Leaf Area Index (LAI) and Normalized Difference Vegetative Index (NDVI) of a plant or plot, thereby enabling the system 10 to test and accurately evaluate factors related to plant performance, including how treatments, such as different seed treatments, affect the LAI and NDVI data acquired from a given plot. Additionally, via the system 10, the researcher can collect and analyze genotypic and/or phenotypic data from organisms in an area and make decisions about which plants should or should not be harvested or how the presence of a certain microbe or animal (e.g. an insect pest) affects plant performance. For example, if an analysis of the genotypic and/or phenotypic data indicate that certain plants in a plot fail to meet a threshold set by a researcher or algorithm for a particular trait, e.g. they do not have a desired height, or do not have a desired yield, or do not have a desired chlorophyll level, or they exceed a desired level of necrosis, etc. then the researcher can flag those plants, e.g. list, or tag them in a database or table. Data flagged in such a way can signal that that the plants in a given area should not be harvested and/or that the data collected from those plants should not be used to make decisions about plant performance, treatment effects, etc. In various other embodiments, the data analysis, treatment decisions, plant selection (or deactivation) decisions can be automated, via implementation of suitable software and algorithms.

Figure 4:
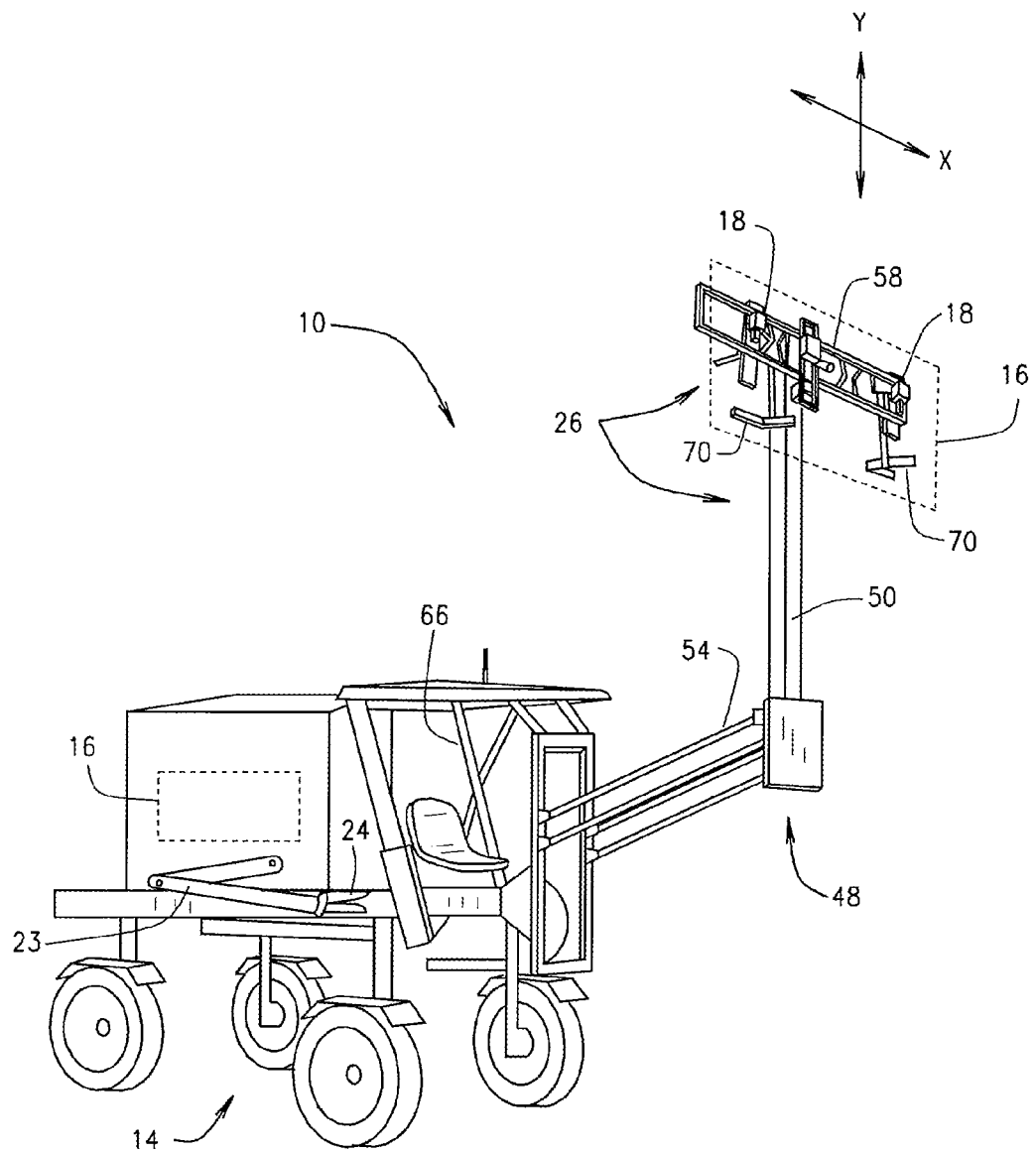
FIG. 4 is an isometric view of the automated crop analysis and treatment system shown in FIG. 1, in accordance with various embodiments of the present disclosure.

Referring now to FIGS. 1, 2 and 4, the imaging device suspension and positioning assembly 26 is structured and operable to adjustably suspend the imaging devices 18 at a desired height along a Y-axis above the ground surface 22 and adjustably position the imaging devices 18 laterally along an X-axis such that each imaging device 18 has field of view 42 having a width W that encompasses one or more plants 46 in a desired number of rows of plants 46. For example, in various embodiments, the imaging device suspension and positioning assembly 26 can comprise a mast and boom subassembly 48 and a horizontal stage 58 mounted to the mast and boom subassembly 48. The mast and boom subassembly 48 includes a boom 54 connected to the mast 50 and the horizontal stage 58 is mounted to the mast 50 or the boom 54, depending on the configuration of the mast 50 and boom 54. In such embodiments, the boom 54 is structured and operable to move the imaging devices 18 vertically up and down along the Y-axis to position the imaging devices 18 at a desired height above the ground surface 22 and the plants 46. The horizontal stage 58 is structured and operable to move each of the imaging devices 18 horizontally back and forth along the X-axis to position the imaging devices 18 at a desired position above the rows of plants 46. Accordingly, the imaging device suspension and positioning assembly 26 is structured and operable to vertically and horizontally adjust the position of the imaging devices 18 so that length L and width W of the field of view 42 for each imaging device 18 encompasses a desired number of plants 46 in a desired number of rows.

In addition to the chassis 30, the mobile platform 14 generally includes an engine and drivetrain (not shown) operable to rotate a plurality of wheels 62 to propel, i.e., impart movement on, the mobile platform 14 through the field of plants 46 and a cab 66 in which a driver/operator can be positioned to operate the mobile platform 14 and the various components of the analytics suite 16 as described herein, and to guide/steer and otherwise control movement of the mobile platform 14 through the field. Alternatively, the mobile platform 14 can be fully automated or remote controlled and not need an onboard driver/operator.

The computer based data processing system 38, as described herein, can be any general-purpose computer comprising electronic memory (shared, dedicated or group), e.g., a hard drive, external flash drive, 'Cloud' based storage, or other electronic memory device, and a processor suitable for executing one or more plant analytics programs, algorithms, routines and/or other code (hereafter referred to simply as the plant analytics software) that utilize the received location data (e.g., the GPS data), the acquired and collected data (e.g., genotype and/or phenotype data, and/or various other image data, and/or tissue samples of the plants, and/or soil samples, and/or environmental readings/samples, etc.), and other captured data to record and analyze the data, map the location of each plant, make plant selection decisions, determine any desired course of action and carry out such actions as the system 10 travels down or over the rows of plants. Alternatively, it is envisioned that the computer based data processing system 38 can comprise any other computer based system or device disposed on the mobile platform 14 or remotely from the mobile platform 14 such as a smart phone, hand held computer, tablet or other computer based system/device that comprises memory and a processor capable of executing the plant analytics software. Additionally, it is envisioned that the computer based data processing system 38 comprise any combination of a general-purpose computer (as described above), any other computer based system or device (as described above), and one or more application specific integrated circuits (ASICs), electronic circuits, combinational logic circuits, field programmable gate arrays (FPGA), or other hardware components that provide various functionality of the system 10, as described herein. Such hardware components can be part of, integrated with, or separate from any of the of the devices of the analytics suite 16. The term code, as used herein, can include software, firmware, and/or microcode, and can refer to one or more programs, routines, functions, classes, and/or objects. The location positioning system 34 can be any location positioning system suitable identifying the location of the system 10, and importantly the location of each plant, sample or data point collected as the system 10 traverses the field collecting the image data, e.g., the location of each color and NIR image data collected, and then communicating the data to the data processing system 38. For example, in various embodiments, the location positioning system 34 can be a high resolution real-time kinematic global positioning system (GPS) receiver operable to receive the satellite positioning data signals and generate a National Marine Electronics Association (NMEA) output that is communicated to the data processing system 38, wherein the GPS receiver receives satellite positioning data signals identifying the geospatial location of the system 10, and importantly the geospatial location of each plant, sample or data point collected as the system 10 traverses the field collecting the image data, e.g., the geospatial location of each color and NIR image data, and then communicating the received data to the data processing system 38.

In various embodiments, at least one imaging device 18 can comprise two charged-couple device (CCD) sensors, one sensor being a full color image sensor and the other being an NIR sensor. In various other embodiments, each imaging device 18 can include a sensor to capture image data in bandwidths other than NIR. Accordingly, in such embodiments, as the system 10 travels through the field, each imaging device 18 captures color image data and NIR image data at periodic intervals, e.g. every two, three, four or more feet, based on the location data received from the location positioning system 34.

Referring now to FIGS. 1, 2, 3 and 4, in various embodiments, operation of the system 10 is as follows. Prior to operation of the system 10 in the field, researchers upload a set of electronic task specific itinerary instructions, e.g., algorithms, programs, routines, functions, etc., to the data processing system 38. The itinerary instructions provide the specific steps and procedures to be implemented in acquiring the specified data for the respective task(s) to be performed by the system 10. As used herein, task will be understood to mean the specific experiment(s) or data gathering operation(s) to be performed by the system 10 at a given time as the system 10 traverses a field. Hence, for each different task (i.e., each different data gather operation) to be performed by the system 10, the researcher can upload different itinerary instructions that provide the specific steps and procedures to be implemented in acquiring the specified data for each different task. For example, the itinerary instructions can specify the one or more genotypic, phenotypic, or environmental characteristics of the plants and/or surrounding area to be measured, and how to collect the data (e.g., what components of the analytics suite 16 and tools 24 will be utilized to acquire the stipulated data). For example, the uploaded itinerary instructions can instruct the system 10 to collect four different types of data in a corn field, e.g., plant height, ear height, nitrogen levels in the soil at the base of the plant, and an approximation of the amount of pollen shed. The instructions can stipulate that plant heights are to be measured from the top of the brace roots to the tip of the tallest tassel, and/or that ear height is to be determined by measuring the distance between two specific points on the top ear only, and/or that each soil sample is to be taken between 15 to 20 cm from the base of the plant and at a depth of 5 to 8 cm, and/or that pollen shed data should only be collected if the tassels have reached a certain point of maturation. Or, as another example, the itinerary instructions can instruct the system 10 to collect data differently based on a characteristic of the environment and/or the status of a plant, microbe, insect, or other living thing detected by the system 10. For example, the system 10 can be instructed to collect pollen count data only if the system 10 detects that the air/gas and/or soil temperature at the time of collection is/are within a certain range of temperatures. Additionally, in various implementation, the instructions can instruct the mobile platform 14 to traverse the field at different speeds based on weather readings, soil moisture levels, plant height, etc., and/or collect data about plant performance only if the plants have reached a certain growth stage or only if they exhibit some characteristic or set of characteristics.

Itinerary instructions could also be uploaded to the data processing system 38 that stipulate about how to collect data on that particular day, for that particular task, or for a particular geospatial point in a field. For example, the itinerary instructions can stipulate how many samples per unit area are to be collected, or that certain plants or plots should be ignored (i.e., deactivated), or whether data should be collected differently in high humidity or temperature versus low humidity or temperatures. Additionally, itinerary instructions can be uploaded that dictate how and what data is to be collected and/or what subsequent course of action should be taken based on real-time analysis of the data collected. For example, if particular data collected and analyzed in real-time does not meet a certain stipulated threshold or fall within a specified range, or meet other stipulated criteria, the uploaded itinerary instructions can instruct the system 10 to repeat the collection of such data, or ignore such data, or modify/adjust such data, or collect one or more types of additional or different data.

Furthermore, in various embodiments, historical and/or current data about the respective field(s), plot(s) and plants can be uploaded to, or accessed by, the data processing system 38. Moreover, in various implementations, the itinerary instructions can instruct the data processing system 38 to take into consideration such historical data previously collected for the respective field(s), plot(s) and plants, and then based on this consideration, require execution of special or modified instructions for acquiring (or not acquiring) the data for particular field(s), plot(s) and/or plants. Therefore, the historical data can be correlated in real-time with the data presently being collected do determine which, if any, courses of action should be implemented by the system 10. For example, plot names or designations, germplasm and/or pedigrees of each plant to be analyzed, row width and planting rates, geospatial data of any plant or point in the field(s)/plot(s), previous or planned treatments, geospatial areas in a field known to be contaminated or previously deactivated, etc., can all be correlated in real-time with the data being collecting, whereby any stipulated course of action can be determined and implemented as a result of the correlation and as stipulated by the itinerary instructions. In various embodiments, any given geospatial point in the field(s)/plot(s) can be assigned values for all the data the system 10 has previously acquired at that point.

Subsequently, the system 10 is positioned adjacent one or more fields comprising one or more plots to be analyzed, and the data processing system 38 executes a calibration routine to calibrate the actual location (e.g., GPS coordinates) of a/the field(s), as described above, such that pre-programmed location (e.g., GPS coordinates) of the field(s), plot(s), row(s), alleys, plants, etc. stored in one or more databases or tables of the data processing system 38 will accurately identify the actual location of the field(s), plot(s), row(s), alleys, head rows, and plants. Thus, the datum or data acquired by the system 10 during operation can be accurately correlated with the geospatial location at which each bit of data is collected. That is, the system 10 can perform a survey of the field(s) to map the boundary of the area to be assayed, set up geospatial waypoints, and collect other environmental data before beginning to collect the various data. As described above, the map can serve as a geo-fence used to indicate when the system 10 should begin or halt data acquisition (i.e. the map indicates how the field is oriented and its dimensions so the system 10 knows when it has finished one row and is properly aligned to begin collecting data for the next row). Hence, the system 10 will use the created map along with the various data and itinerary instructions provided, as described above, to ensure the system 10, i.e., the data processing system 38, is properly correlating the data being collected with the correct plant, plot and field location.

Subsequently, the system 10 proceeds to a boarder of a field with the wheels 62 aligned with two corresponding furrows. Next, the boom 54 and stage 58 are operated to position the imaging devices 18 along the X and Y axes to position the imaging devices 18 at a desired height and location above the rows where the field of view 42 of each imaging device 18 has a length L and width W that will include any desired number of rows of plants 46 and number of plants 46 within each row. Once the imaging devices 18 are positioned and aligned the following occur (the following list is only exemplary and is non-limiting in the number and order of system 10 operations): 1) the system 10 begins to move along the rows; 2) the data processing system 38 is operated to begin execution of the plant analytics software; 3) the location positioning system 34 receives position data indicative of the starting location of the system 10 within the field; 4) each imaging device 18 is operated (via control of the data processing system 38) to simultaneously capture initial image data, e.g., a full color image and an initial NIR image, and communicate the image data to the data processing system 38; 5) any other components of the analytics suite 16, e.g., the LIDAR 19, illumination meter/light sensor 20, necessary to acquire the stipulated data are initialized and begin collecting data and communicating the data to the data processing system 38; and 6) the location positioning system 34 constantly receives position data (e.g., GPS coordinates) indicating the real-time location of the system 10 and plants 46 within the field as each bit of data is collected, and communicates the location data (e.g., the GPS coordinates) to the data processing system 38 to be recorded, whereafter the data processing system ties, assigns or associated, each bit of data acquired with the respective location data (e.g., the GPS coordinates). The acquired data for analysis and location data (e.g., the GPS coordinates) can be stored in the data processing system 38, or transmitted to one or more separate database or computer based system in any way known or anticipated in the art.

As described above, the imaging devices 18 are positioned and aligned to have a field of view 42 that encompasses one or more plants 46 in the desired number of rows. More specifically, once the imaging devices 18 are positioned and aligned to have the field of view width W, the data processing system 38 can calculate a length L of the field of view 42 for the imaging devices 18. Subsequently, as the system 10 moves through the field the data processing system 38, via execution of the plant analytics software, determines when the system 10, and particularly the imaging devices 18, have moved a distance L-x, wherein x is a predetermined overlap distance. Particularly, the distance L-x is utilized as a periodic interval at which the imaging devices 18 will be operated by the data processing system 38 and will capture sequential sets of image data as the system 10 moves through the field. Because the periodic interval of the image data capture is L-x, wherein L is the length of the field of views 42, each set of image data captured will comprise overlapping image data with the image data captured at the previous periodic interval L-x. Accordingly, simultaneous image data will be captured of all the plants 46 in the entire field with no gaps in the collected image data. This imaging process is described in further detail in published PCT Application PCT/US2012/060729, titled Plant Stand Counter, filed Oct. 18, 2012, based on U.S. Provisional Application 61/549,320, filed Oct. 20, 2011, and corresponding US National Phase application Ser. No. 14/353,036, filed Apr. 21, 2014, the disclosure of each being incorporated by reference herein in their entirety.

As described above, in various embodiments, the system 10 further includes one or more illumination detection devices 70, e.g., one for each imaging device 18, that are utilized to adjust the light intensity of the image data, e.g., color and NIR 2D, 3D or line-scan image data, collected according to the light intensity, i.e., the amount of sunlight, present as each set of image data is captured. Therefore, the light intensity for all the image data captured as the system 10 traverses the field will be normalized and substantially equal. Such image normalization, improves the consistency of the image data, e.g., the color and NIR image data, resulting in more reliability of a defined response across a broader range of illuminance intensities. This broader range means less effect on the variation of image response from cloud cover induced variations in the light intensity. The illumination detection device 70 can comprise any device suitable for acquiring such illuminance intensity data, such as light intensity reference cards that are positioned within the field of view 42 of each respective imaging device 18 or the illuminance meter/light sensor 20, e.g., a photometer, mounted on the crop analysis and treatment system 10 in any suitable location where the illumination detection device(s) 70 has/have constant exposure to the respective sunlight and will not be overshadowed, at any time, by any other part, structure or component of the crop analysis and treatment system 10.

In such embodiments, the illumination detection device(s) 70 is/are operable to provide real-time illuminance information, i.e., real-time light intensity data, to the data processing system 38 for the image normalization process. Particularly, the illumination detection device(s) 70 measure(s) light intensity and the data processing system 38 correlates the illuminance values (lux) in real-time to the corresponding image data that were acquired at the same point in time.

During the operation phase, as the system 10 traverses the field, the illumination detection device(s) 70 capture(s) light intensity values, i.e., illuminance data, for each set of image data captured, e.g., color and NIR image data. The light intensity values generated by the illumination detection device(s) 70 is/are collected in real-time for each set of color and NIR image data and stored in memory of the data processing system 38. Subsequently, in real-time, the data processing system 38, utilizes the captured light intensity values to predict a relative reflectance corresponding to each set of image data captured. Utilizing the predicted relative reflectance, in real-time, the data processing system 38 then normalizes each set of image data captured, via execution of the plant analytics software. Thereafter, via execution of the plant analytics software, the normalized image data can be used, along with data captured from other components of the analytics suite 16, e.g., the LIDAR 19, to determine such things as the number of plants of a selected type growing in the field, and/or the height of each plant, and/or the leaf area index (LAI) of each plant, and/or any other desired genotype or phenotype traits, characteristics, data and/or information of any plant or group of plants.

Figure 5:
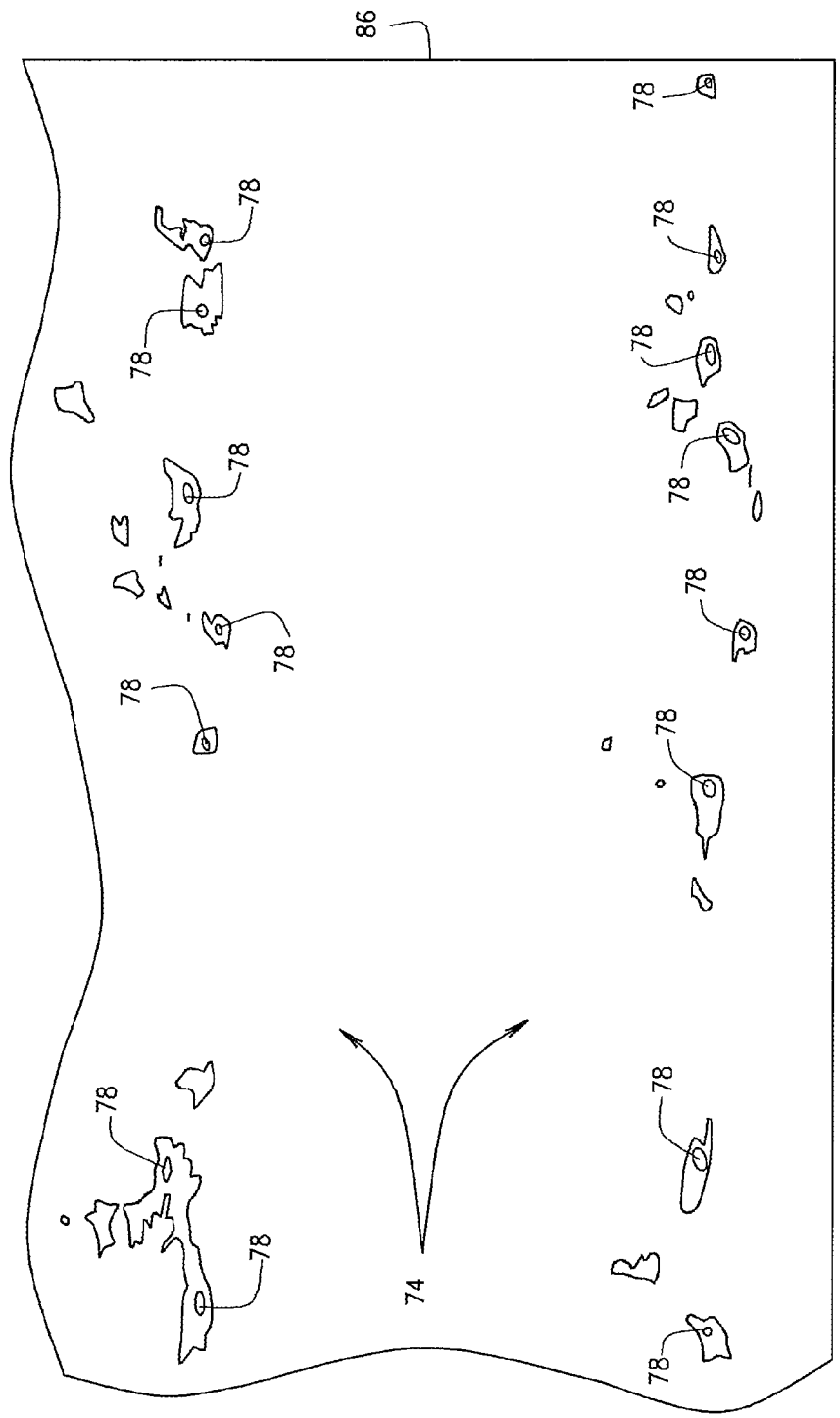
FIG. 5 is a rendering of a portion of a false color image of a plot of plants, showing a portion of two of a plurality of rows of plants in the plot, generated by the automated crop analysis and treatment system shown in FIG. 1, in accordance with various embodiments of the present disclosure.
Figure 6:
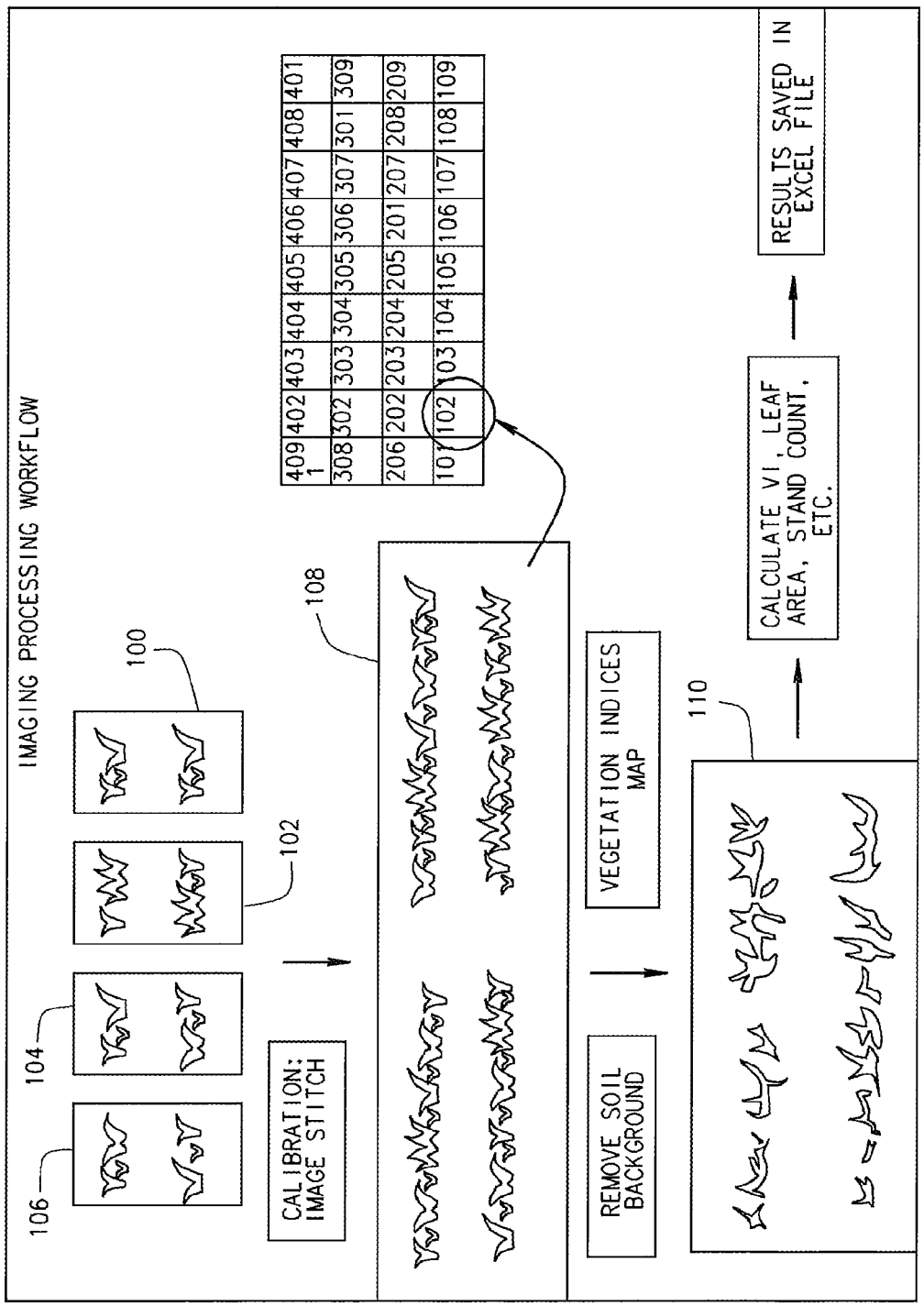
FIG. 6 is an exemplary illustration of an imaging processing workflow implemented via execution of a plant analytics software implemented by the automated crop analysis and treatment system shown in FIG. 1, in accordance with various embodiments of the present disclosure.

For example, referring now to FIGS. 5 and 6, as described above, as the system 10 moves through the field 86, each set of image data captured, e.g., color and NIR image data, at the periodic intervals can be communicated to the data processing system 38 where the sets of image data from each imaging device 18 are normalized, stored and analyzed via execution of the plant analytics software. For example, in various implementations, execution of the plant analytics software calculates a pixel by pixel color ratio between normalized color and NIR image data for each set of image data captured. That is, the algorithm takes each pixel from the color image data and compares it to the same pixel (e.g., a pair of co-registered pixels) from the NIR image data and calculates a color ratio between the two, which provides a numeric value for each pixel. This numeric value is sometimes referred to as a normalized difference vegetative index (NDVI), which is correlated to the amount of chlorophyll contained in the various parts of the plant, and therefore, can be used to detect the level of chlorophyll contained in various parts of a plant and/or detect and/or quantify the amount and distribution of vegetation in an image. In various embodiments, the NDVI calculation is made on a pixel by pixel basis utilizing the following equation:

$$(NIR-Red)/(NIR+Red)$$

where NIR is the value of the near-infrared monochrome pixel and Red is the red value of the color pixel. Alternatively, the same computation can be made using the green value for each color pixel. This NDVI calculation is made for each image data set captured by each imaging device 18.

Subsequently, the plant analytics software can utilize the NDVI data to determine various phenotypic and/or genotypic traits/characteristics, data and/or information for any single plant and/or any group of plants. For example, in various embodiments, the plant analytics software can utilize the NDVI value for each pixel to generate a false color image 74 (shown in FIG. 5) for each set of image data. Particularly, execution of the plant analytics software assigns a particular color to specific NDVI values such that each pixel is assigned a color based on the respective NDVI value, thereby creating a color image, i.e., the false color image 74, utilizing the NDVI values for each pixel. For example, in various implementations, low NDVI values, i.e., low ratio values, indicate responses for soil, water and non-living plant material and are assigned light neutral background colors in the false color image 74. Conversely, the higher NDVI values indicate areas of the plants with higher chlorophyll density and are respectively assigned darker colors that contrast with the background colors in the false color image 74. One skilled in the art would readily understand that the chlorophyll density, as indicated by the NDVI values, is related to the amount of chlorophyll in the cells of the respective plants 46, but can also be related to the density of the plant matter for the respective plants 46.

In such examples, the false color image 74 can be utilized to illustrate the location of the highest level of chlorophyll in plants within each set of image data. And more particularly, because areas with higher levels of chlorophyll will be represented as certain colors in the false color image 74, the false color image 74 can be utilized to identify a desired plant distinguishing characteristic 78 (e.g., a whorl 78 of each), thereby indicating the locations of each plant within each set of image data. In various implementations, the execution of the plant analytics software can utilize a determined minimum threshold value for NDVI values to remove values that are not indicative of chlorophyll containing matter, e.g., soil, water, non-living plant material, other plant material or residue (e.g., silage), or other undesired crop plant matter, (e.g. weeds or volunteers), such that only the pixels that represent the desired plants are recognized.

For example, in embodiments wherein the desired plant to be counted is corn, it is known that corn plants have a stronger NDVI response, i.e., a higher NDVI value, as they mature. Hence, the minimum threshold value will be increased for more mature corn plants. Therefore, in various exemplary implementations, prior to the V4 stage of corn, the corn plants 46 are detected by simply setting a selected minimum threshold for the NDVI values to filter out NDVI values below the threshold, and then counting the resulting contiguous pixel regions generated in the false color image 74, each contiguous pixel region indicating a plant 46 to be counted. The growth stage is information that is provided by a system operator, also referred to as analytics software herein. However, starting at the V4 stage, corn plants 46 will show a characteristic NDVI response at their whorls 78 that can be identified and counted via the false color image 74. Particularly, the whorls 78 in corn plants 46 act as visible light traps such that the color data values will be much reduced, but the corresponding NIR values are not reduced. Hence, the change in the NDVI values, i.e., the sharp increase in NDVI values, at the whorl 78 produces the particular plant distinguishing characteristic 78 in the false color image 74 that is indicative of a corn plant.

Furthermore, execution of the plant analytics software can stitch together the images (e.g. stitching the color images and the NIR images to extract a false color image 74) for all sets of image data for each imaging device 18 using the image data set overlap, described above, to generate a comprehensive false color image 74 of the entire field, or of one or more particular plots within the field.

Although the system 10 is exemplarily illustrated as having two imaging devices 18, each having a field of view length L and width W sized to include two rows of plants 46 such that the system 10 will simultaneously capture the image data for four rows of plants 46, the system is not limited to this exemplary configuration. It is envisioned that the system 10 can be configured to simultaneously capture the image and other desired data for one, two, three, five, six, seven, eight or more rows of plants 46, utilizing one, two, three, four or more imaging devices 18, each having a field of view length L and width W that encompasses one, two, three, four or more rows 98 of plants 46, and other data collecting components of the analytics suite 16.

As described above, the system 10 can utilize data acquired/captured/collected from the imaging devices 18 and other components of the analytics suite 16, e.g., the LIDAR 19, the ion selective electrodes 24, the optical and/or electrical conductivity sensors 24, the DNA detection sensors 24, to not only identify and count the plants 46 in a field 82, but to analyze the plants 46 in real-time as the system 10 moves through the field 82. For example, in various embodiments, the system 10 can be utilized to provide information regarding such things as nitrogen levels within the plants 46, insect infestation of the plants 46, spatial arrangement of the plants 46, plant height, corn ear height, plant color, and time-related data for determining plant vigor ratings, leaf area index (LAI), plant morphology and biomass estimates, iron deficiency chlorosis, foliar diseases, stalk diseases, weed pressures, nitrogen use efficiency (NUE), water use efficiency (WUE), geo-referenced location of individual plants within a field, soil quality and health, plant stress due to nutrients, environment, and/or disease, etc.

For example, in various embodiments, the system 10 can collect data, metrics and other information for determining the following, non-limiting list of plant genotypic and phenotypic information, structure, attributes, characteristics and qualities utilizing the various components and other onboard sensors of the analytics suite 16 and the articulating arms 23 and tools 24 of the system 10.

| Plant Characteristic/Attribute To Be Determined | Device, System, Sensor, etc. To Be Used. |
| --- | --- |
| Plant Height | LIDAR |
| Stand Count | Multi-spectral camera |
| NUE | Hyper-spectral camera |
| WUE | Hyper-spectral camera |
| Foliar diseases | Multi-spectral camera |
| Stalk disease | NIR spectrometer |
| Plant morphology and biomass | 3D camera |
| Iron deficiency chlorosis | Multi-spectral camera |
| Weed pressure | Multi-spectral or RGB camera |

-continued

| Plant Characteristic/Attribute To Be Determined | Device, System, Sensor, etc. To Be Used. |
| --- | --- |
| Soil quality - ph, organic matter, cation exchange capacity, nitrogen, potassium, phosphorous, texture, water holding capacity, salinity, temperature | Automated soil sampling - ion selective electrodes, optical or electrical conductivity |
| Soil health - soil pathogen detection | Automated soil sampling - DNA detection sensor |
| Soil health - microbial community profile | Automated soil sampling - DNA detection sensor |

Subsequent to the determination of the genotypic, phenotypic, or other desired data, execution of the plant analytics software can determine a course of action to be implemented by the system 10 based on predetermined database information, lookup table data, subroutines, etc. stored in electronic memory accessible by the data processing system 38, and/or any electronic itinerary instructions uploaded by a researcher, as described above. For example, in various instances, based on the analysis of the acquired data and any uploaded itinerary instructions, execution of the plant analytics software can determine whether a soil sample should be collected, and/or a tissue sample of one or more plants should be collected, and/or an air sample should be collected, and/or further image and/or LIDAR data could be acquired, and/or a specific pesticide or herbicide should be sprayed on a particular group of plants 46. Moreover, the system 10 is structured and operable to carry out a respective course of action, via the onboard devices, systems, mechanisms, and apparatus such as the robotic articulating arms 23, tools 24, solution applicators 25, and other onboard sensors of the analytics suite 16.

Referring now to FIGS. 1 through 6, as described above, execution of the plant analytics software provides real-time feedback (e.g., to a remotely located researcher, or to automated components of the data processing system 38 located locally on the mobile platform 14 or at a remote location from the mobile platform 14) regarding all the data the system 10 is acquiring. In various embodiments, a quality control process can be implemented wherein the data can be reviewed and analyzed to make sure it corresponds, based on data currently and/or previously collected about the location with what is expected to be acquired from the respective field(s), plot(s) and/or plants. If any data appears (to the remote researcher or components of the data processing system 38) to be skewed or spurious from what is expected, e.g., chlorophyll content data of a particular plot or group of plants 46 is skewed from historical chlorophyll data recorded for that particular plot or group of plants 46, the research can flag the presently acquired data as possibly erroneous, and/or deactivate the data, and/or send instructions to the system to acquire additional data. Additionally, if data values are acquired for locations where no plants should appear (i.e. no seeds were planted there), the quality control process can determine that the system 10 may be misaligned and/or that it is collecting data in the wrong manner or from the wrong area of the field or plot. Furthermore, the quality control process can indicate if rows or plants were skipped, and/or that one or more plant is damaged, and/or that the mobile platform 14 is moving too fast or too slow, and/or that there is too much or insufficient lighting, and/or that the part of the plant or organ targeted for data collection is not present, e.g. the plant is too short or that the particular organ in question has not sufficiently developed.

In various embodiments, the quality control process can include hardware diagnostics wherein the performance and operation status of one or more of the components of the analytics platform 16 and/or other devices and instruments of the system 10 is monitored and communicated to the to a remotely located researcher, or to automated components of the data processing system 38 located locally on the mobile platform 14 or at a remote location from the mobile platform 14, whereby corrective action or repair can instituted if necessary. Hence, operation of the system 10 and execution of the plant analysis software provides real-time quality control of all data, as the data is being collected. That is, the quality control process and software can be utilized to make real-time adjustments (via a researcher, or automatically utilizing one or more quality control algorithms) or use this information later to weight data subsequently collected based on how confident the researchers are that the data collected accurately reflects the traits or characteristic being measured.

Via operation of the system 10, execution of the plant analysis software, and execution of the quality control process, as described herein, various other acquired data and information can be monitored, analyzed and/or compared with historical data to verify the quality of the data collected, e.g., accuracy and validity of the data collected. For example, the processed image data can be analyzed to verify whether the image data includes undesirable overlaps, gaps, black images, over-saturation, buffered, or corrupted or missing data, including misalignments between color and NIR band images. If such undesirable instances are detected, the corrective course of action can be to assign empty image data to those planting locations. Additionally, a percentage of data loss can be monitored and if an excessive amount of data loss is detected, e.g., greater than 5%, the data for the respective locations can be flagged as not usable for making any subsequent analytic determinations. Furthermore, plot length can be monitored such that if acquired data indicated that a plot is too long or too short, e.g., if the acquired data indicates that the plot is greater than 10% longer or 10% shorter than expected, the data for the respective plot can be deactivated.

Still further, the growth stage of the plants can be monitored and if a respective plant has not reached a stipulated growth stage, the data for the respective plant can be deactivated. For example, if the growth stage of a corn plant is determined to be less than V2, the data acquired for that particular corn plant can be deactivated. Further yet, if data acquired for a particular plot indicates that the plot had too many or too few rows, or than the separation of the rows is too large or too small, or that the width of one or more of the rows is too wide or too narrow, the data for the respective plot can be deactivated. Still further yet, if acquired data indicates that the average height of the plot is too tall or too short the data acquired for particular plant(s) can be deactivated, e.g., flagged as not usable for making any subsequent analytic determinations. Further still yet, if the acquired data indicates that image data for one or more plants has an incorrect, e.g., insufficient, number of pixels, or the image data is corrupted, or the image resolution is not above a stipulated threshold, or is not deterministic, the data for the respective plants or plots can be deactivated.

More particularly, as a result of the various data capturing and collection devices of system 10, the acquired data provides overlapping activation criteria, which can co-dependently or independently produce a deactivation of data. Specifically, or each data acquisition source of the analytics suite 16, e.g., the cameras 18, the location positioning system 34, the sensors 90, 92 and 94, etc., separate activation flags are maintained and transmitted along with derived metrics. In various implementations, ground truth inputs such as plot length, alley length, row spacing and range count can establish the basis of comparison to the acquired and analyzed data. Data validation and pre-processing can be performed in the several stages, which together can handle common quality issues such as completely absent content, excessive calibration panel coverage by shadow, over-exposure artifacts, corruptions (present, but unreadable source data, be it image or image meta), LIDAR filtering for stationary/reversed data sweeps and positional anomalies which lead to extreme overlaps and or gaps between images. In most instances, the affected data is marked as un-trusted and removed (for LIDAR) or replaced by a gap (for imaging) in the reconstructions that follow. The direct consequence of such altered content is increased probability of traits deactivation for the particular plot. In various implementations, plots can be divided out of a fully stitched column, one per camera, and subject to attribute filters which will deactivate excessively abnormal plots. For example, if the data loss for particular image data is of over 5%, the respective data can be deactivated. Given data can pass various quality control criteria yet still be deactivated due to its failure to meet one or more other criteria. Or, in order for given data to deactivated, it can be stipulated that such data must fail two or more quality control criteria. For example, when LIDAR is present, image resolutions can be required to be derived using the fusion of the LIDAR readings, wherein any plot that contains one or more images that have no related LIDAR heights can be deactivated.

Figure 9:
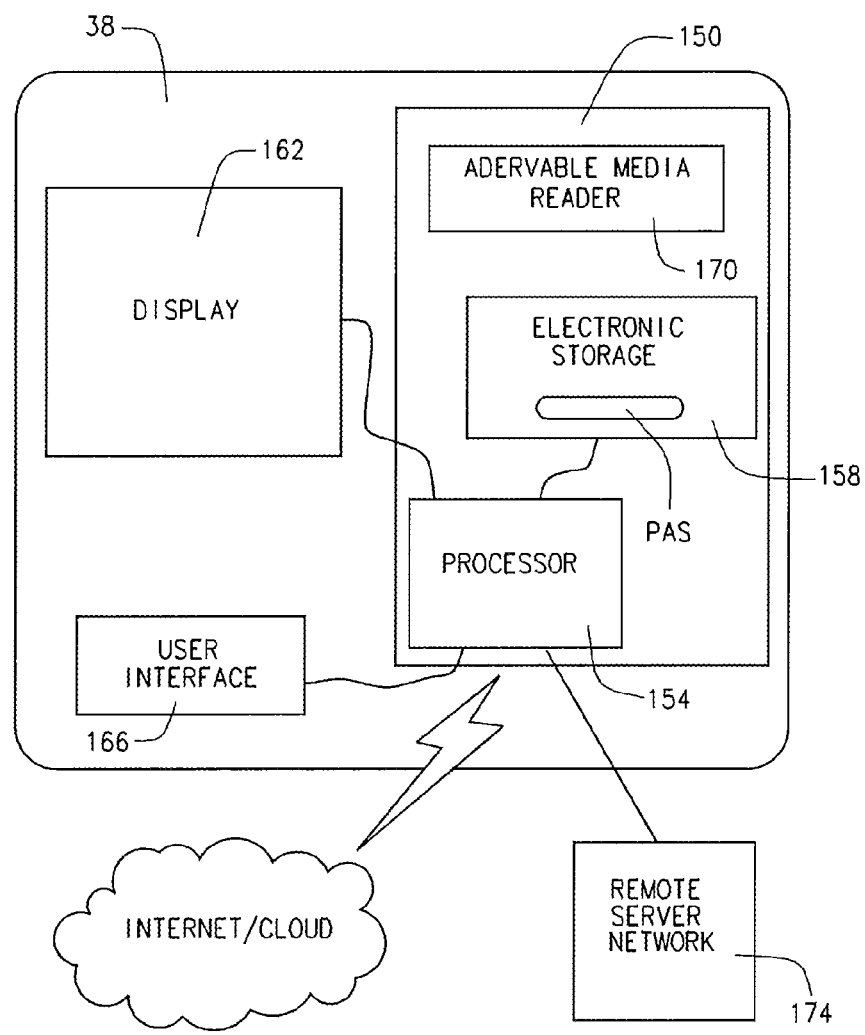
FIG. 9 is a block diagram of a date processing system of the system shown in FIG. 1, in accordance with various embodiments of the present disclosure.

Referring now to FIG. 9, as described above, the automated crop analysis and treatment system 10 includes and is controlled by the data processing system 38. Particularly, operation of the system 10, as described herein, is controlled by the execution the plant analysis software and associated algorithms and/or routines described herein. As described above, the data processing system 38 includes one or more computer based devices. More particularly, in various embodiments, the data processing system 38 is a computer based system that includes one or more computers 150 that can be located locally on the mobile platform 14 and/or remotely from the mobile platform 14. Each computer 150 includes at least one processor 154 suitable to execute at least a portion of the plant analysis software (PAS) to control various automated functions and operations of the system 10, as described herein. Each computer 150 additionally includes at least one electronic storage device 158 that comprises a computer readable medium, such as a hard drive or any other electronic data storage device suitable for storing such things as all or portions of the plant analysis software, various other algorithms and digital information, data look-up tables, spreadsheets and databases, etc. Furthermore, in various embodiments, the data processing system 38 can include at least one display 162 for displaying such things as information, data and/or graphical representations, and at least one user interface device 166, such as a keyboard, mouse, stylus, and/or an interactive touch-screen on the display 166. For example, a remotely located computer 150 can include a display 166 and user interface 166, whereby a researcher can monitor data as it is acquired and perform the quality control processes described above. In various embodiments, each computer 150 can include a removable media reader 170 for reading information and data from and/or writing information and data to removable electronic storage media such as floppy disks, compact disks, DVD disks, zip disks, flash drives or any other computer readable removable and portable electronic storage media. In various embodiments the removable media reader 170 can be an I/O port of the respective computer 150 utilized to read external or peripheral memory devices such as flash drives or external hard drives.

In various embodiments, the data processing system 38, e.g., one or more of the computers 150, can be communicatively connectable to a remote server network 174, e.g., a local area network (LAN), via a wired or wireless link. Accordingly, the data processing system 38 can communicate with the remote server network 174 to upload and/or download data, information, algorithms, software programs, and/or receive operational commands. Additionally, in various embodiments, the data processing system 38 can be structured and operable to access the Internet and/or Cloud based memory to upload and/or download data, information, algorithms, software programs, etc., to and from the data processing system 38.

Referring now to FIGS. 1 through 9, as described herein, the general operation of the system 10 comprises data analyzed during (i.e., in real-time) and/or after acquisition of the data via execution of the plant analysis software, wherein the plant analysis software can (the following list is only exemplary and is non-limiting in the number and order of software operations): 1) automatically stitch multiple images together to form an accurate mosaic image for analysis, e.g., a false color image 74, in various implementations, a plurality of false color images 74 can be generated for the same plot or plats using image data from acquired at different viewing angles; 2) extract phenotypic and/or genotypic trait or characteristic values from the data collected in the field, e.g., provide phenotypic and/or genotypic trait or characteristic values for each plot, and/or for individual plants 46, and/or for particular leaves of plants 46, and/or for particular environmental or growing area conditions (e.g. the areas in the images occupied by plants and their locations relative to the areas where seeds were not planted (alleys and rows) or patches of bare ground), and/or for particular geospatial conditions, etc.; 3) acquire and monitor environmental conditions, geospatial conditions, etc.; 4) use historical data collected and stored to provide real-time quality control processes that compare the data collected with expected data sets, or control data sets, to verify the accuracy of the presently acquired data, whereby researchers can review the results and institute or perform automated or manual quality control actions to compensate for any detected anomalies or spurious data; and 5) automatically upload the results into one or more database, wherein the uploaded data can include the location data (e.g., the GPS data), the phenotypic and/or genotypic trait or characteristic, the quality control information, field and time conditions for all data point acquired, any other desired meta data, etc.

Hence, the various acquired data, per plot and/or per plant, is available in databases for researchers to review. The acquired data per plant and/or plot from each location can be compared within the location data and across multiple locations to select and/or evaluate the performance of individual plants, different treatments, germplasms, growing conditions or growing prescriptions, etc. Furthermore, analysis of the acquired and stored data can reveal data patterns. For example, data indicating a possible issue with data corresponding to a particular plant trait in one area of a field can reveal that data in other parts of the field, or data for other traits in the same part of the field, could be spurious, that data collected from the area can be statistically be statically weighted during subsequent analysis to account for the effects caused by the source of the observed pattern. For example, users of the presently disclosed systems and methods will be better able to recognize when the actual reason a particular germplasm failed to meet a certain threshold for selection was due to variation in some factor unrelated to genetics or proscribed treatments. For example, by accounting for these patterns, a germplasm that would be eliminated for poor performance in one area of the field using previous methods, can now be flagged as a false negative (or positive, depending on the trait) because an issue was identified with that part of the field that could be skewing the results in a spurious manner. Also, the detection and characterization of non-random variations, observed via data patterns, allows users of the presently disclosed systems and methods to identify and analyze more carefully regions of a field where the quality of data is suspect and potentially spurious.

FIG. 6 illustrates an exemplary imaging processing workflow implemented via execution of the plant analytics software. Upon initiation of the plant analytics software, the system 10 begins capturing successive image data shown in images 100, 102, 104 and 106. Subsequently, the images 100, 102, 104 and 106 are calibrated, e.g., normalized based on illumination data collected, and stitched together to generate image 108, which is identified, tagged and/or correlated with a specific plot of plants. Next, the soil and other background data is removed from the image 108 to provide vegetation indices map 110. Utilizing the vegetation indices map 110, execution of the plant analytics software can determine such plant information as vegetative index, Leaf Area Index (LAI), Normalized Difference Vegetative Index (NDVI), stand count, and/or any other indicator of plant health or plant performance.

Figure 7:
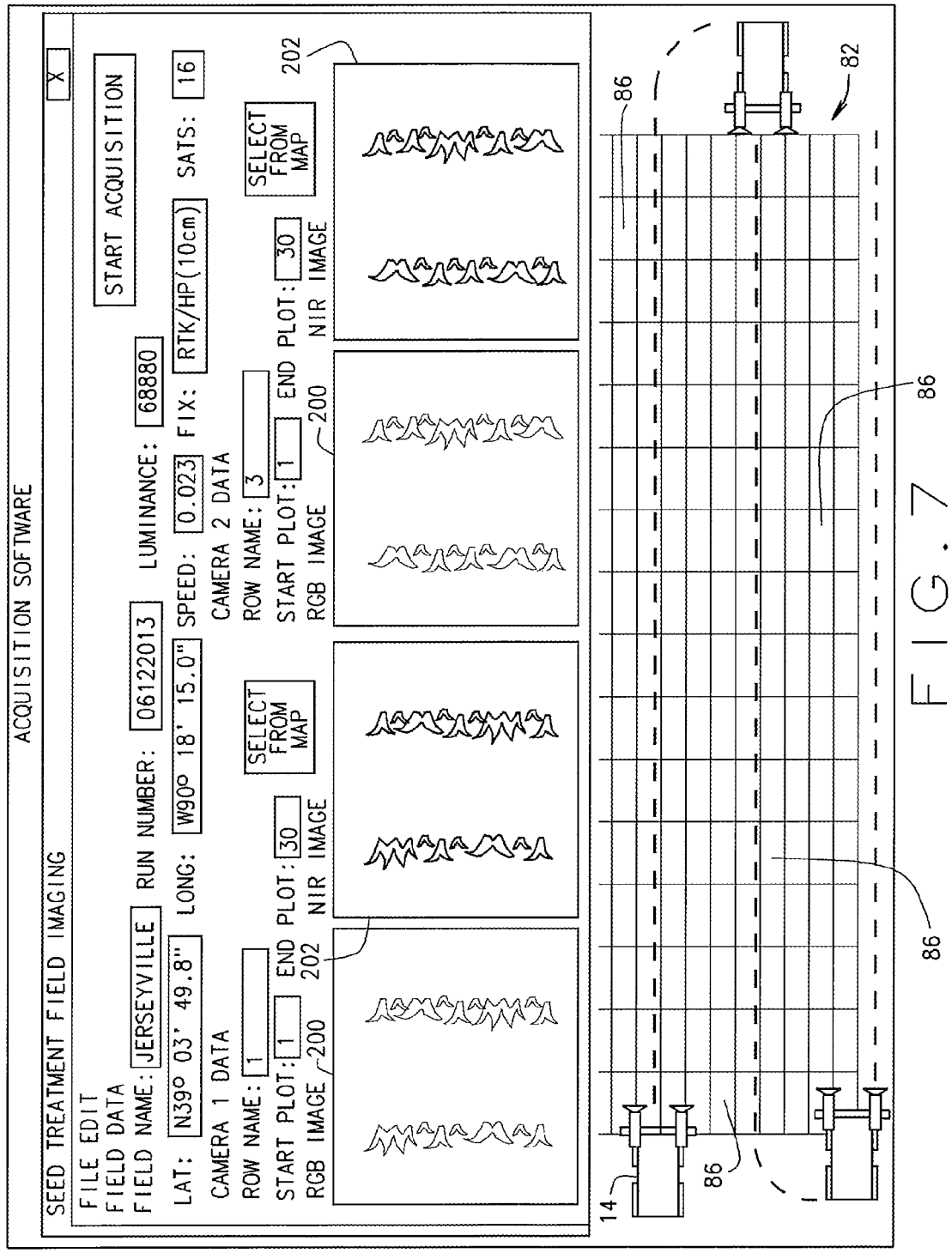
FIG. 7 is an exemplary illustration of a screenshot of the plant analytics software, in accordance with various embodiments of the present disclosure.

FIG. 7 is provides an exemplary illustration of a screenshot displayed in real-time (i.e., simultaneously with the actual data acquisition and operation of system 10) to a researcher (located locally on the mobile platform 14 or remotely from the mobile platform 14 anywhere in the world) via execution the plant analytics software. As exemplarily illustrated, the researcher is provided a real time the location (e.g., the GPS position) of the mobile platform 14 as it traverses plots 86 in the field 82. As also exemplarily illustrated, the researcher is provided real-time images of the image data being acquired by two imaging devices 18, e.g., the color images 200 and the NIR images 202 for each imaging device 18.

EXAMPLES, TEST RESULTS AND EXPERIMENTS

Figure 8E:
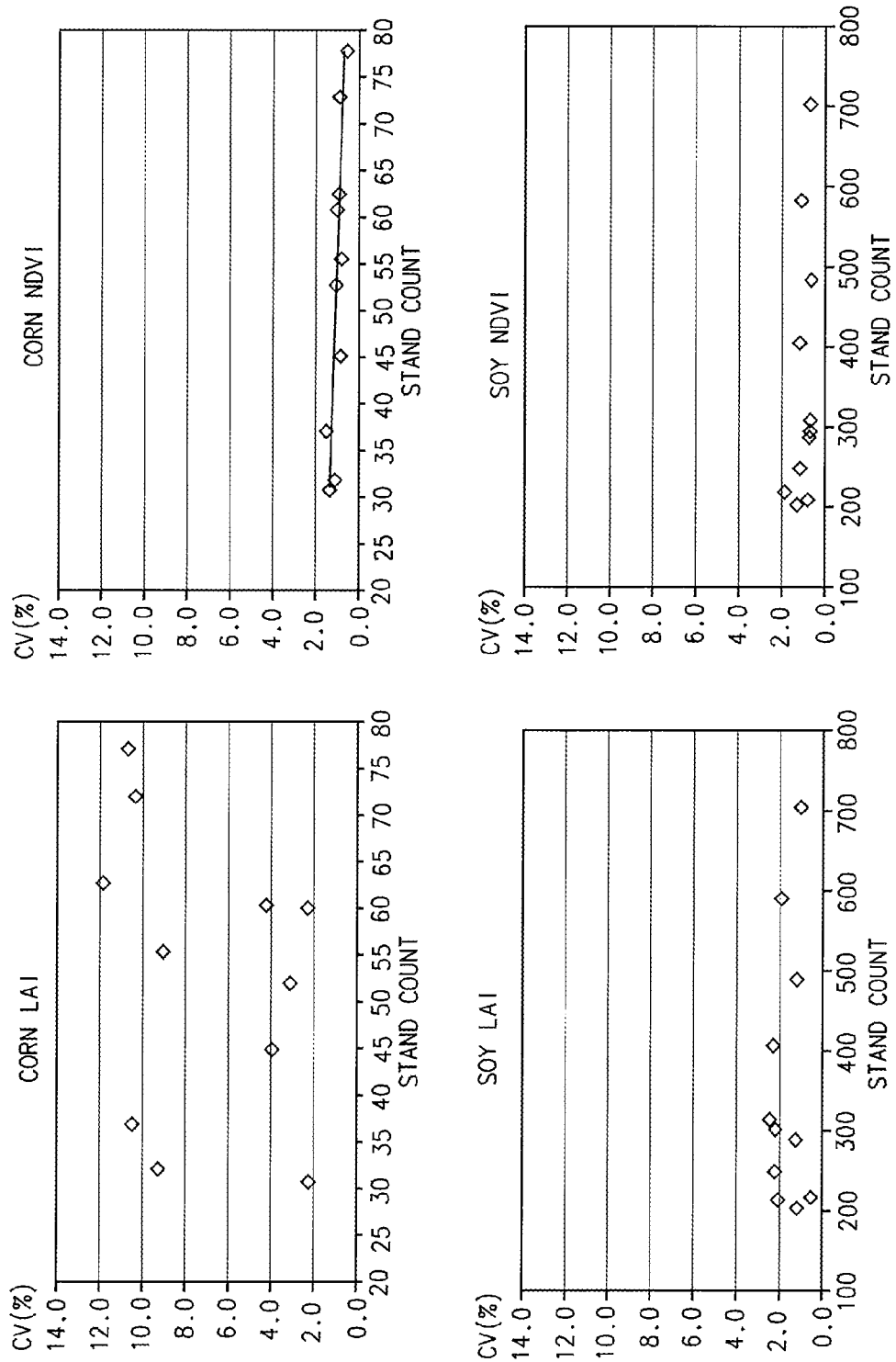

Referring now to FIGS. 8A through 8G, the following is an exemplary description of, and results from, an imaging validation study of the automated crop analysis and treatment system 10, described above. Data from twenty-four, 2 row plots of soybean and twenty-four, 2 row plots of corn were used in this study. Half of the plots were unaltered for the course of the study and half of the plots were altered by reducing the stand count for consecutive images. The plot lay-out is shown in FIG. 8A with the altered plots 86 highlighted. Images were taken in a serpentine fashion through the plots 86 starting with plot A for every image set.

The plots 86 were intentionally planted at different densities. The densities ranged from 32 to 91 plants 46 in corn and 175 to 705 plants 46 in soy. Individual plot density values are indicated FIG. 8B. Correlation coefficients were calculated by image run across the 24 plots per crop. Correlation coefficients will be understood to mean a coefficient that illustrates a quantitative measure of some type of correlation and dependence, meaning statistical relationships between two or more variables or observed data values. For example, a correlation coefficient can be a statistic that measures the relationship between two variables, e.g., values can range from 0 (no correlation) to 1 (perfect correlation). The results are illustrated in FIG. 8C. All correlation coefficients above 0.40 are significant (P<0.05). The repeatability of imaging of the system 10 was tested in a field environment by repeated imaging of twelve plots 86 of soybeans and twelve plots 86 of corn. Nine sets of consecutive images were taken for each of the soybean plots. Eight sets of images were taken for each of the corn plots. The data from the 7th se of corn images were not available for analysis. The repeatability of the coefficient of variation (CV) for LAI and NDVI were calculated by plot and then pooled across plots. The results of the plot analysis are shown in FIG. 8D. Two plots, D for corn and T for soy, had considerably higher CV for LAI than the other plots for the same crop. Both of these plots were at the end of the field 82 where the mobile platform 14 would be making a turn for another pass and may have been damaged by the multiple passes. The LAIs were lesser on both plots for the later images. The plots surrounding these 2 plots that had plants removed did not show patterns that would indicate that plants were pulled from incorrect plots. The two plots with high CVs for their respective crop were excluded from the remainder of the analyses reported.

Within a crop, the CVs for LAI were not found to be a function of the plot density as measured by stand counts. The CV for NDVI was not a found to be a function of stand count for soy, but a significant linear relationship was found for corn, as illustrated in FIG. 8E. For corn, the NDVI CV decreased with increasing density but all CVs were found to be <2%. The data from all plots (except Corn D and Soy T) were pooled for an overall estimate of assay repeatability.

Figure 8G:
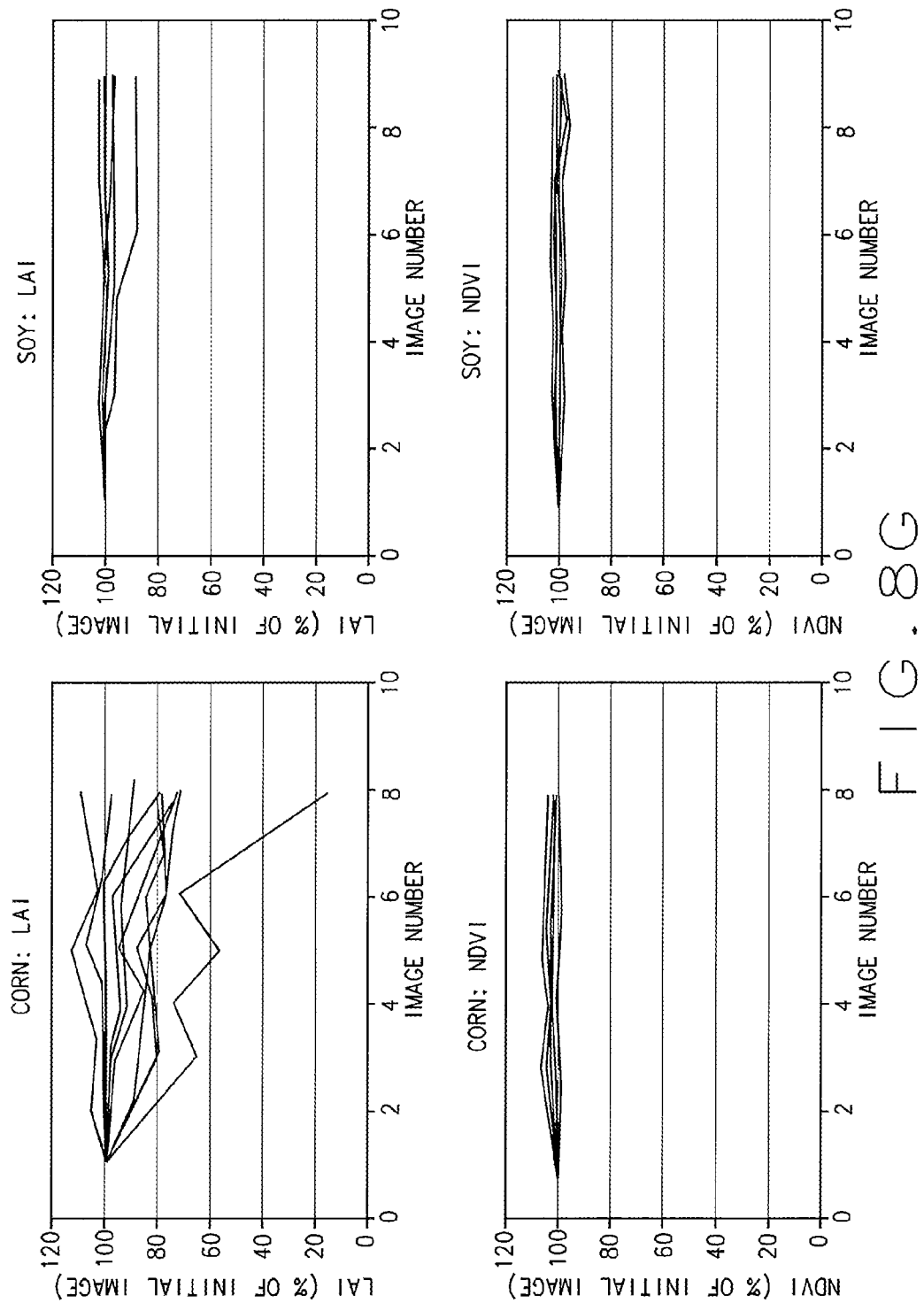

As illustrated in FIG. 8F, greater LAI CVs for the corn plots can be partially explained by the lower mean value than the soy plots. Further investigation of greater CV for corn LAI was made by examining trends over the time of the image. The graphs shown in FIG. 8G present the trends over time for the repeated images on the corn and soy plots. All plots were standardized to have starting values of 100 for comparison purposes. The two plots that have been excluded from the analysis are included in the graphs.

For NDVI, no individual corn plots were found to have a significant linear change with time. Across all corn plots, the positive slope of 0.03 was non-significant. Four of the soy plots had significant decreases in NDVI with time. Across all soy plots, the negative slope of −0.16 was significant (P<0.05). For LAI, six of eleven corn plots had significant linear decreases with time and over all plots the slope of −1.72 was significant (P<0.05). For soy, six of eleven plots had significant linear decreases with time and the slope of −0.31 across all plots was significant (P<0.05). Based on the hypotheses that the decrease in LAI with time is due to normal daily variations, the CVs reported are good estimates of the assay repeatability. If the decrease is due to an artificial altering of the plots by repeated traffic then the trend could be accounted for in the CV calculation. FIG. 8H shows the CVs after accounting for the measured trend in image time across all plots.

Moreover, testing of the system 10 has illustrated that the system 10 can be utilized to accurately, effectively and efficiently detect the effects of spraying crops with an herbicide. Particularly, soy bean experiments have been performed to illustrate that the system 10 can accurately differentiate between untreated control soy plants and all soy bean plants treated with various treatments utilizing LAI and NDVI values acquired and calculated using the system 10, as described above, and planting density accurately determined using the LAI and NDVI data. Furthermore, testing has illustrated that the system 10 can determine which type treatment a particular plot received.

In other experiments, the system 10 has proven to be able to evaluate the effect of a cucumber seed coating on germination and above-ground plant development utilizing plant stand counts, LAI and NDVI acquired and calculated using the system 10, as described above.

In another experimental study to determine the operation, accuracy, viability, repeatability, dependability and usefulness of the automated crop analysis and treatment system 10, described above, interpretation of the acquired data accurately indicated that certain areas of a field were 'ponding', i.e., did not have proper water drainage, and therefore the respective acquired data could be deactivated and corrective action could be implemented. Specifically, real-time review, analysis and interpretation by a researcher of data acquired during operation of the system 10 indicated that in certain areas/plots the plants were less mature, whereupon further analysis the researcher determined that the soil moisture was above an acceptable level/threshold, thereby indicating 'ponding' in those areas/plots. More specifically, during real-time review, analysis and interpretation of the acquired data by a researcher, the researcher noticed that the NDVI values (determined via the system 10 and execution of the plant analysis software) for certain areas/plots of the analyzed field were low (e.g., significantly below the NDVI values for the rest of the field, or below a particular threshold), indicating that the respective plants were less mature. In response to the low NDVI values, the researcher examined the real-time image data (e.g., image data 200 and 202 shown in FIG. 7) whereby the researcher was able to determine that there was ponding in those particular areas/plots. Therefore, the researcher was able to deactivate the data acquired from those areas/plots.

Hence, operation of the system 10 and analysis of the data acquired allows researcher to not only compare from one plot to the data from another plot, but also compare data from one plot to the data from a plurality or all of the plots in the field, thereby effectively turning the entire field into a "control" that can be used to more accurately analyze and interpret the data, and accurately, repeatedly and dependably, e.g., among other things, 1) obtain data and information regarding any desired genotypic, phenotypic, or environmental information, structure, attributes, characteristics and qualities of the plant(s) and/or surrounding area; 2) analyze in real-time the data so gathered, including comparing the data collected about a subject or location at different times to detect and characterize change in the subject or location over time; 3) determine, in real-time, a desired course of action based on the analysis; 4) carryout the determined course of action; 5) implement quality control process to insure the accuracy and reliability of the data; and 6) record and store the captured data, collected samples, resulting analysis, course of action taken, and mapped location for future reference and use.

As described above, although the system 10 has been illustrated as having the computer based data processing system 38 disposed on mobile platform 14, in various embodiments, as described above, the computer based data processing system 38 can be a multi-part system having only a portion of the multi-part system disposed on the mobile platform 14. For example, in various embodiments, the data processing system 38 can include a first part disposed on the mobile platform 14 and one or more other parts disposed remotely from the mobile platform 14, e.g., a laboratory located anywhere in the world. Exemplarily, the first part could be structured and operable to execute a first portion of the plant analytics software to collect/capture the color and NIR image, and the second part(s) could be structured and operable to execute a second portion(s) of the plant analytics software to analyze the collected/captured color and NIR image data and generate the false color image 74, determine responsive courses of action, implement such courses of action, perform quality control function, etc., as described above.

The description herein is merely exemplary in nature and, thus, variations that do not depart from the gist of that which is described are intended to be within the scope of the teachings. Such variations are not to be regarded as a departure from the spirit and scope of the teachings.

What is claimed is:

1. A method for performing in-field data acquisition regarding one or more characteristic of at least one of a plurality of plants within a field, said method comprising:
    mapping, in real-time, a geospatial location of at least one plant growing in a field, utilizing a global positioning system (GPS) of a mobile analytics system, as a mobile platform of the mobile analytics system traverses the field;
    acquiring, in real-time, various data associated with the at least one plant as the mobile platform traverses the field utilizing various devices of an analytics suite of the mobile analytics system, wherein the data comprises at least image data of the at least one plant acquired via at least one imaging device of the analytics suite, wherein acquiring, in real-time, various data for the at least one plant as the mobile platform traverses the field further comprises:
        collecting at least one of plant tissue samples from selected plants, air samples from at least one location within the field, and soil samples from at least one location within the field, and
        analyzing the acquired data to determine at least one environmental characteristic at at least one location in the field;
    associating and storing, in real-time, location data with at least one bit of data acquired, via a data processing system of the mobile analytics system;
    analyzing, in real-time, the acquired data, via the data processing system, to determine at least one of:
        at least one genotypic characteristic of the at least one plant,
        at least one phenotypic characteristic of the at least one plant; and
        at least one plant performance characteristic of the at least one plant;
    determining, in real-time, via the data processing system, whether a responsive course of action is needed to be implemented by the mobile analytics system based on the analyzed data;
    carrying out, in real-time, via the mobile analytics system, the determined responsive course of action when it is determined that a responsive course of action is needed to be implemented;
    recording and storing, via the data processing system, historical data each time the mobile analytics system operationally traverses the field, the historical data comprising:
        the image, phenotypic and genotypic data for each respective traversal of the field;
        data regarding the collected samples for each respective traversal of the field;
        the resulting data analysis for each respective traversal of the field;
        any course of action determined and taken for each respective traversal of the field; and
        the location data for each respective traversal of the field; and
    utilizing the historical data during subsequent real-time data analyzes by the data processing system during subsequent operational traverses of the field by the mobile analytics system.

2. The method of claim 1 further comprising:
    mapping the field, prior to operationally traversing the field to acquire data, by mapping the location of at least the four corners of the field; and
    calibrating the historical location data to be used during the present operational traversal of the field utilizing the field mapping location data.

3. A method for performing in-field data acquisition regarding one or more characteristic of at least one of a plurality of plants within a field, said method comprising:
    mapping, in real-time, a geospatial location of at least one plant growing in a field, utilizing a global positioning system (GPS) of a mobile analytics system, as a mobile platform of the mobile analytics system traverses the field;
    acquiring, in real-time, various data for the at least one plant as the mobile platform traverses the field utilizing various devices of an analytics suite of the mobile analytics system, wherein the data comprises at least image data of the at least one plant acquired via at least on imaging device of the analytics suite, wherein acquiring, in real-time, various data for the at least one plant as the mobile platform traverses the field further comprises:
        collecting at least one of plant tissue samples from selected plants, air samples from at least one location within the field, and soil samples from at least one location within the field; and
        analyzing the acquired data to determine at least one environmental characteristic at at least one location in the field;
    associating and storing, in real-time, location data with each bit of data acquired, via a data processing system of the mobile analytics system;
    analyzing, in real-time, the acquired data, via the data processing system, to determine at least one of:
        at least one genotypic characteristic of the at least plant, and
        at least one phenotypic characteristic of the at least one plant,
            wherein the analysis of the acquired data comprises utilizing historical data acquired and stored during at least one previous operational traversal of the field by the mobile analytics system;
    determining, in real-time, via the data processing system, whether a responsive course of action is needed to be implemented by the mobile analytics system based on the analyzed data; and carrying out, in real-time, via the mobile analytics system, the determined responsive course of action when it is determined that a responsive course of action is needed to be implemented; and recording and storing, via the data processing system, the historical data each time the mobile analytics system operationally traverses the field, the historical data comprising:
- the image, phenotypic and genotypic data for each respective traversal of the field;
- data regarding the collected samples for each respective traversal of the field;
- the resulting data analysis for each respective traversal of the field;
- any course of action determined and taken for each respective traversal of the field; and
- the location data for each respective traversal of the field.

4. The method of claim 3 wherein acquiring, in real-time, various data for the at least one plant as the mobile platform traverses the field further comprises acquiring at least one of: genotypic data from the at least one plant, phenotypic data from the at least one plant, plant performance data from the at least one plant, data related to at least one of soil health and composition from a location in the field; and chemosensory data from a location in the field.

5. The method of claim 3 further comprising:

mapping the field, prior to operationally traversing the field to acquire data, by mapping the location of at least the four corners of the field; and calibrating the historical location data to be used during the present operational traversal of the field utilizing the field mapping location data.

* * * * *